US006438413B1

(12) United States Patent
Taheri

(10) Patent No.: US 6,438,413 B1
(45) Date of Patent: Aug. 20, 2002

(54) BIOPOTENTIAL SENSOR ELECTRODE SYSTEM

(75) Inventor: Babak A. Taheri, San Francisco, CA (US)

(73) Assignee: Integrated Biosensing Technologies, Redwood City, CA (US)

( * ) Notice: Subject to any disclaimer, the term of this patent is extended or adjusted under 35 U.S.C. 154(b) by 0 days.

(21) Appl. No.: 09/532,323

(22) Filed: Mar. 21, 2000

Related U.S. Application Data
(60) Provisional application No. 60/179,302, filed on Jan. 31, 2000.

(51) Int. Cl.[7] .............................. A61B 5/04; A61B 5/05
(52) U.S. Cl. ....................... 600/547; 600/372; 128/903
(58) Field of Search ................................ 600/547, 502, 600/372, 391, 392, 395, 396; 607/149; 128/903

(56) References Cited

U.S. PATENT DOCUMENTS

| | | | |
|---|---|---|---|
| 3,882,846 A | 5/1975 | Fletcher et al. | 128/2.06 E |
| 3,967,628 A | 7/1976 | Vredenbregt | 128/417 |
| 4,141,351 A | 2/1979 | James et al. | 128/2.06 R |

(List continued on next page.)

FOREIGN PATENT DOCUMENTS

| | | | | |
|---|---|---|---|---|
| GB | 2227322 A | * | 7/1990 | 600/538 |

Primary Examiner—Kevin Shaver
Assistant Examiner—Charles Marmor, II
(74) Attorney, Agent, or Firm—Dorsey & Whitney LLP

(57) ABSTRACT

A method and apparatus for biopotential sensing and stimulation are provided including a sensory component, a biopotential sensor electrode, and a biopotential sensory electrode system. The sensory component includes a first layer of electrically conductive material coupled among a biopotential signal source and a dielectric layer. A second layer of electrically conductive material is coupled among the dielectric layer, resistive elements, a charge balancing current source and sink, and circuits of the associated biopotential electrode. The biopotential sensor electrode includes the sensory component, conditioning components, an interface, and a power source. Stimulation components may also be included to provide stimulation signals to the biopotential signal source. The interface transfers signals to external instrumentation using wireless or wired connections. The power source includes batteries, solar cells, and telemetry power sources. The biopotential sensory electrode system includes electrode arrays and a receiver section that transfers biopotential signals among the biopotential signal source and external instrumentation and equipment. A reference link among the sensor electrodes of an array is provided by a coupling that includes current injection to a surface of the biopotential signal source, or a common wire to all electrodes.

35 Claims, 20 Drawing Sheets

U.S. PATENT DOCUMENTS

| | | | | |
|---|---|---|---|---|
| 4,259,965 A | | 4/1981 | Fukuda et al. | 128/640 |
| 4,275,744 A | | 6/1981 | Thornton et al. | 128/731 |
| 4,313,443 A | | 2/1982 | Lund | 128/642 |
| 4,332,566 A | | 6/1982 | Mazeski et al. | 434/178 |
| 4,505,799 A | | 3/1985 | Baxter | 204/416 |
| 4,564,022 A | | 1/1986 | Rosenfeld et al. | 128/748 |
| 4,583,549 A | | 4/1986 | Manoli | 128/640 |
| 4,603,704 A | | 8/1986 | Mund et al. | 128/784 |
| 4,643,193 A | | 2/1987 | DeMarzo | 128/639 |
| 4,658,826 A | | 4/1987 | Weaver | 128/640 |
| 4,669,479 A | | 6/1987 | Dunseath, Jr. | 128/640 |
| 4,705,049 A | | 11/1987 | John | 128/731 |
| 4,706,679 A | | 11/1987 | Schmidt et al. | 128/639 |
| 4,736,751 A | | 4/1988 | Gevins et al. | 128/732 |
| 4,753,246 A | | 6/1988 | Freeman | 128/731 |
| 4,757,825 A | * | 7/1988 | Diamond | 600/535 |
| 4,763,659 A | | 8/1988 | Dunseath, Jr. | 128/640 |
| 4,763,660 A | * | 8/1988 | Kroll et al. | 600/391 |
| 4,862,359 A | | 8/1989 | Trivedi et al. | 364/413.05 |
| 4,865,039 A | | 9/1989 | Dunseath, Jr. | 128/640 |
| 4,865,566 A | | 9/1989 | Rasmussen | 439/825 |
| 4,874,500 A | | 10/1989 | Mandou et al. | 204/412 |
| 4,928,704 A | | 5/1990 | Hardt | 128/732 |
| 4,967,038 A | | 10/1990 | Gevins et al. | 128/644 |
| 4,975,175 A | | 12/1990 | Karube et al. | 204/403 |
| 4,981,141 A | | 1/1991 | Segalowitz | 128/696 |
| 5,003,978 A | | 4/1991 | Dunseath, Jr. | 128/640 |
| 5,038,782 A | | 8/1991 | Gevins et al. | 128/644 |
| 5,119,816 A | | 6/1992 | Gevins | 128/644 |
| 5,156,591 A | | 10/1992 | Gross et al. | 604/20 |
| 5,168,874 A | | 12/1992 | Segalowitz | 128/639 |
| 5,307,818 A | | 5/1994 | Segalowitz | 128/696 |
| 5,458,141 A | | 10/1995 | Neil | 128/641 |
| 5,511,553 A | | 4/1996 | Segalowitz | 128/696 |
| 5,617,865 A | * | 4/1997 | Palczewska | 600/301 |
| 5,645,063 A | | 7/1997 | Straka, Jr. | 128/641 |
| 5,724,984 A | | 3/1998 | Arnold et al. | 128/696 |
| 5,775,332 A | * | 7/1998 | Goldman | 600/587 |
| 5,788,633 A | | 8/1998 | Mahoney | 600/382 |
| 5,862,803 A | * | 1/1999 | Besson et al. | 600/508 |
| 5,868,671 A | | 2/1999 | Mahoney | 600/382 |
| 6,033,370 A | * | 3/2000 | Reinbold et al. | 600/595 |
| 6,117,077 A | * | 9/2000 | Del Mar et al. | 600/301 |
| 6,201,980 B1 | * | 3/2001 | Darrow et al. | 600/347 |
| 6,295,466 B1 | * | 9/2001 | Ishikawa et al. | 600/509 |

\* cited by examiner

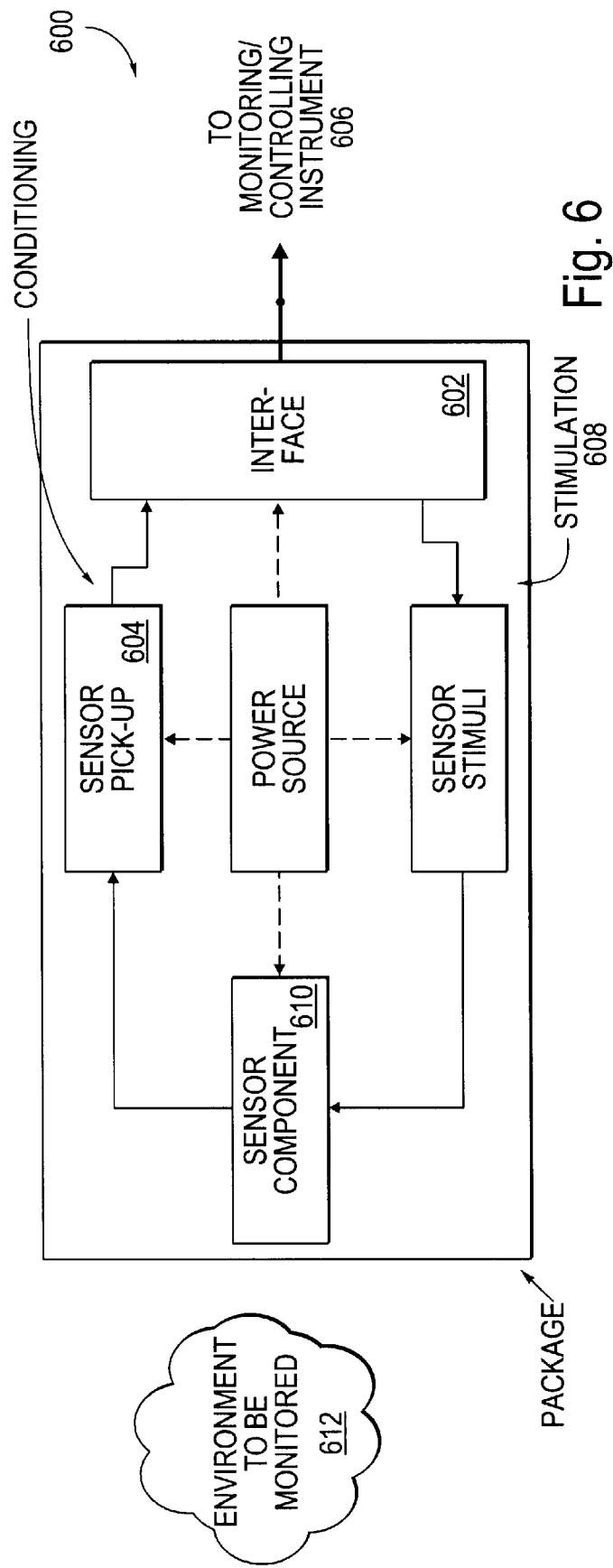
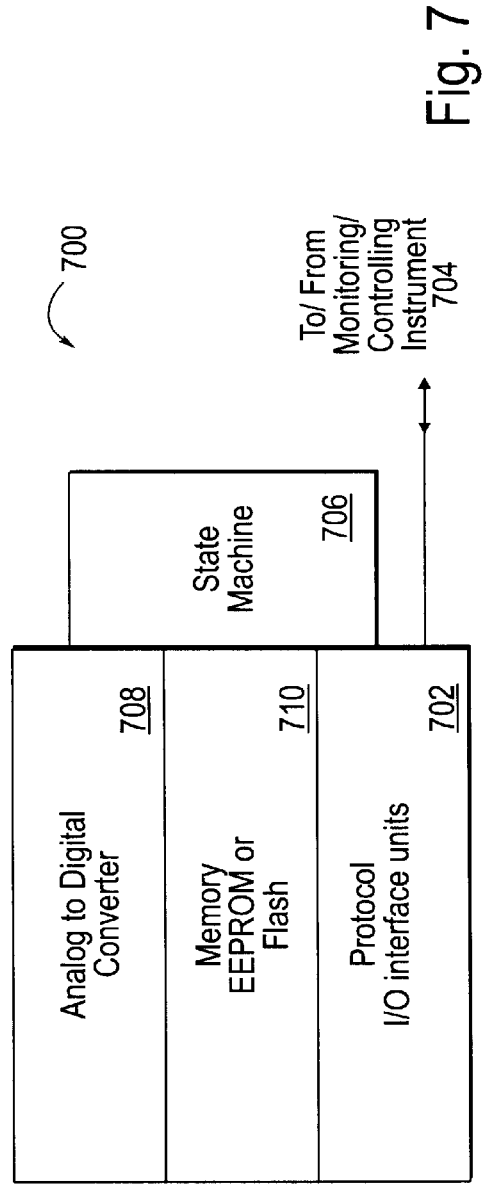

BIOPOTENTIAL SENSOR ELECTRODE SYSTEM

RELATED APPLICATION

This application claims the benefit of U.S. Provisional Application No. 60/179,302, filed Jan. 31, 2000.

GOVERNMENT LICENSE RIGHTS

The United States Government may have certain rights in some aspects of the invention claimed herein, as the invention was made with United States Government support under grants 1R43NS36870-01A1 and R43MH55410-01 awarded by the National Institutes of Health.

BACKGROUND OF THE INVENTION

1. Field of the Invention

This invention relates to the field of biopotential sensors. In particular, the invention relates to surface electrodes.

2. Description of the Related Art

Typical biopotential sensing/stimulating systems are used to gather a growing variety of biopotential signal types or information from subjects or patients. These sensing/stimulating systems are also used to stimulate the patient with a known signal such that skin impedance and other information can be sensed from the subjects or patients. Typical biopotential sensing/stimulating systems include two types of subsystems, biopotential sensors and the associated external monitoring systems or instrumentation. While the medical information capable of being extracted from this biopotential information has increased significantly with advances in medical science and technology, the usefulness of these systems remains as a limiting factor in patient treatment because of deficiencies of the typical biopotential sensing/stimulating systems.

Regarding the biopotential sensor/stimultor subsystem, biopotential sensors/stimulators can generally be categorized as being invasive or non-invasive. Invasive sensors are implanted surgically, and are used for accurate isolation of potential sources during sensing and/or delivery of a stimulating signal in to a specific target location. The invasive sensors/stimulators can usually be applied to peripheral nervous systems (i.e., axons or muscles) or to introcerebral sites as in brain research.

Non-invasive sensors/stimulators, also referred to as surface, skin, or scalp electrodes and/or sensors, are applied to the skin surface. These electrodes are typically connected to the surface of the skin via an electrolyte or gel, hence they are also referred to as wet surface electrodes, or wet electrodes. Wet surface electrodes are commercially available and are routinely used in the clinics and research labs. The preference for wet surface electrodes is due in part to the relatively low manufacturing cost of wet electrodes, and historically proven technology. Furthermore, the wet surface electrodes are passive devices that can be used for both sensing and stimulating, since all the necessary electronics and intelligence resides in the external monitoring systems or instruments.

One class of surface electrodes does not use electrolytes. These electrodes, referred to as active electrodes, employ an impedance transformation at the sensing site via active electronics. The active electrodes are subdivided into two electrode types, dry electrodes and insulated electrodes. The dry electrode has a metal in direct contact with the skin which is followed by an impedance converting amplifier. The insulated electrode is capacitively coupled to the skin via a dielectric which is followed by an impedance converting amplifier.

Research results for active electrodes have demonstrated that both dry and insulated electrodes are comparable to wet electrodes for sensing or receiving electrocardiogram (ECG or EKG) signals. However, typical active dry and insulated electrodes do not exhibit the same consistency and signal to noise ratio (SNR) as the wet electrodes. In addition, the typical non-invasive active electrodes have been used for signal sensing purposes only and not stimulating. While the research has focused on ECG signals, there are numerous other biopotential signal types to which the application of active electrodes would be desirable but has yet to be demonstrated.

Efforts to realize active insulated electrodes have included significant research and development in the area of sensor dielectrics. A number of materials have been investigated for thin-film capacitor fabrication in sensors of the active hybrid electrodes. Some of the materials typically considered for use include silicon monoxide (SiO), silicon dioxide ($SiO_2$), silicon nitride ($Si_3N_4$), Diamond like Carbon (DLC), and tantalum pentoxide ($Ta_2O_5$). In practice, deposited dielectric films thinner than 500–700 Angstroms (Å) have a fairly high pinhole density and the yields are poor. Pinholes lead to resistive shorts between the electrodes (in the vicinity of each other) and increase the leakage current. Thick dielectric films, or films with a thickness greater than approximately 20,000 Å also may exhibit problems because of the high internal stress levels found in these films. High compressive forces cause the films to peel off; however, large tensile forces can be relieved by crazing, or the production of fine cracks in the film. These factors thus may limit the thickness of the dielectric material to between 800 Å and 10,000 Å.

While both silicon monoxide and silicon dioxide are good insulators for electrical isolation, their behavior as a barrier to sodium ions (Na+) is poor. In addition, these two materials require high temperatures in order to form high quality films with few pinholes. Tantalum pentoxide also can suffer from high-temperature deposition requirements and low breakdown voltage.

The insulated electrodes with dielectrics currently in use are not practical because of breakage, scratched surfaces, and inconsistency. Therefore, there is a need for an electrode dielectric material having a number of specific properties. The properties desired include: low reaction with sodium chloride (NaCl) for biocompatibility and sensor protection; low deposition temperature (approximately less than 500 degrees Celsius) to be compatible with electrode material; high dielectric constant for obtaining a large capacitance in a small area; high dielectric strength (resulting in high breakdown voltage) for electrostatic protection; moderate leakage resistance for impedance matching to the amplifier; and, oxidation rate 30 times slower than that of silicon.

Regarding electrode monitoring subsystems, a typical electrode monitoring system consists of the following components: (1) an array of wet electrodes attached to the monitoring environment; (2) electrode cables for coupling each of the wet electrodes to instrumentation; (3) a cable converter box for receiving the electrode cables; and, (4) a monitoring system connected to the cable converter box with a series of cables. The typical electrode signal path from the sensor to the monitoring system is through unshielded cables of approximately 3 to 6 feet in length. These cables typically degrade the signal-to-noise-ratio (SNR) of the recording system and increase motion artifacts. In addition, the cables confine the movement of the subject as well as impose a health hazard in monitoring systems. Consequently, there is a need for an electrode monitoring system that does not require the patient to be wired to the monitoring system, a system that eliminates the need for electrode cables, the cable converter box, and the monitoring cables.

Wireless telemetry systems in general are classified as active or passive. Active telemetry systems are used for telemetry over longer distances. Therefore, typical active telemetry systems require a power source in both transmitter and receiver sections. The power source is primarily used to operate active devices such as transistors that form the circuits for these systems. The factors that influence the distance of communications include the available power, frequency of operation, and antenna size.

Typical telemetry for monitoring systems use either infrared red (IR) or radio-frequency (RF) links. These systems consist of several wet electrodes mounted on a cap and connected via cables to a transmitter section. The transmitter section consists of transmitter circuitry, a power unit, IR light emitting diodes or a large antenna, voltage converters/ multiplexers, and a microcontroller unit. The transmitter section requires very high bandwidth and additional signal processing circuitry in order to provide digitized and time multiplexed data for transmission. As such, the size and weight of the transmitter section in these telemetry systems prevents them from being mounted on the cap with or in the electrodes. Therefore, the transmitter section is placed on a belt strap which is attached to the subject. Thus, the cables along with the size, weight, and power consumption of the transmitter section limit the application of these systems.

While a number of RF telemetry systems have been deployed, most have been discontinued for use in electrode monitoring applications because of these limitations. Furthermore, IR telemetry systems have also found limited applications due to the size and poor SNR resulting from signal attenuation due to light reflections, and the amount of light that couples into the detectors.

Recently, in the field of local area networking and telephony, wireless systems have been introduced that utilize RF and spread spectrum techniques. These systems in their current state are not suitable for use in electrode monitoring systems without major modification, for a number of reasons. As an example, since these systems provide only a single transmitter channel, they would require additional signal processing and multiplexing if used in an electrode monitoring system. Furthermore, an increase in the number of electrodes would increase the power consumption, and thus the size of the transmitters, inhibiting their use for high resolution electrode recording. Thus, there is a need for a micro-telemetry system that eliminates cables that connect a subject to a monitoring system and is small in size and weight for ease of attachment and carrying.

SUMMARY OF THE INVENTION

A method and apparatus for biopotential sensing and stimulation are provided including a sensory component, a biopotential sensor electrode, and a biopotential sensory electrode system.

The sensory component includes a first layer of electrically conductive material coupled among a biopotential signal source and a dielectric layer. A second layer of electrically conductive material is coupled among the dielectric layer, resistive elements, a charge balancing current source and sink, and circuits of the associated biopotential electrode.

The biopotential sensor electrode includes the sensory component, conditioning components, an interface, and a power source. The sensory component is coupled among the biopotential signal source and the conditioning components. The conditioning components couple conditioned signals to the interface, which is configured to transfer signals to external instrumentation. The signal transfer occurs over wireless or wired connections. Stimulation components may also be coupled among the sensory component and the interface to provide stimulation signals to the biopotential signal source. The power source is coupled among the sensory component, the conditioning components, and the interface, and includes batteries, solar cells, and telemetry power sources.

The biopotential sensory electrode system includes at least one electrode array. The electrode array includes the biopotential sensor electrodes and a receiver section that transfers biopotential signals among the biopotential signal source and external instrumentation and equipment. A reference link among the biopotential sensor electrodes of an array is provided by a coupling that includes current injection to a surface of the biopotential signal source, or via a common wire to all electrodes.

The descriptions provided herein are exemplary and explanatory and are provided as examples of the claimed invention.

BRIEF DESCRIPTION OF THE FIGURES

The accompanying drawings illustrate embodiments of the claimed invention. In the drawings:

FIG. 6 is a functional block diagram of a hybrid sensor electrode of an embodiment.

FIG. 7 is a functional block diagram of an interface for a hybrid sensor electrode digital interface of an embodiment.

DETAILED DESCRIPTION

Figure 1:
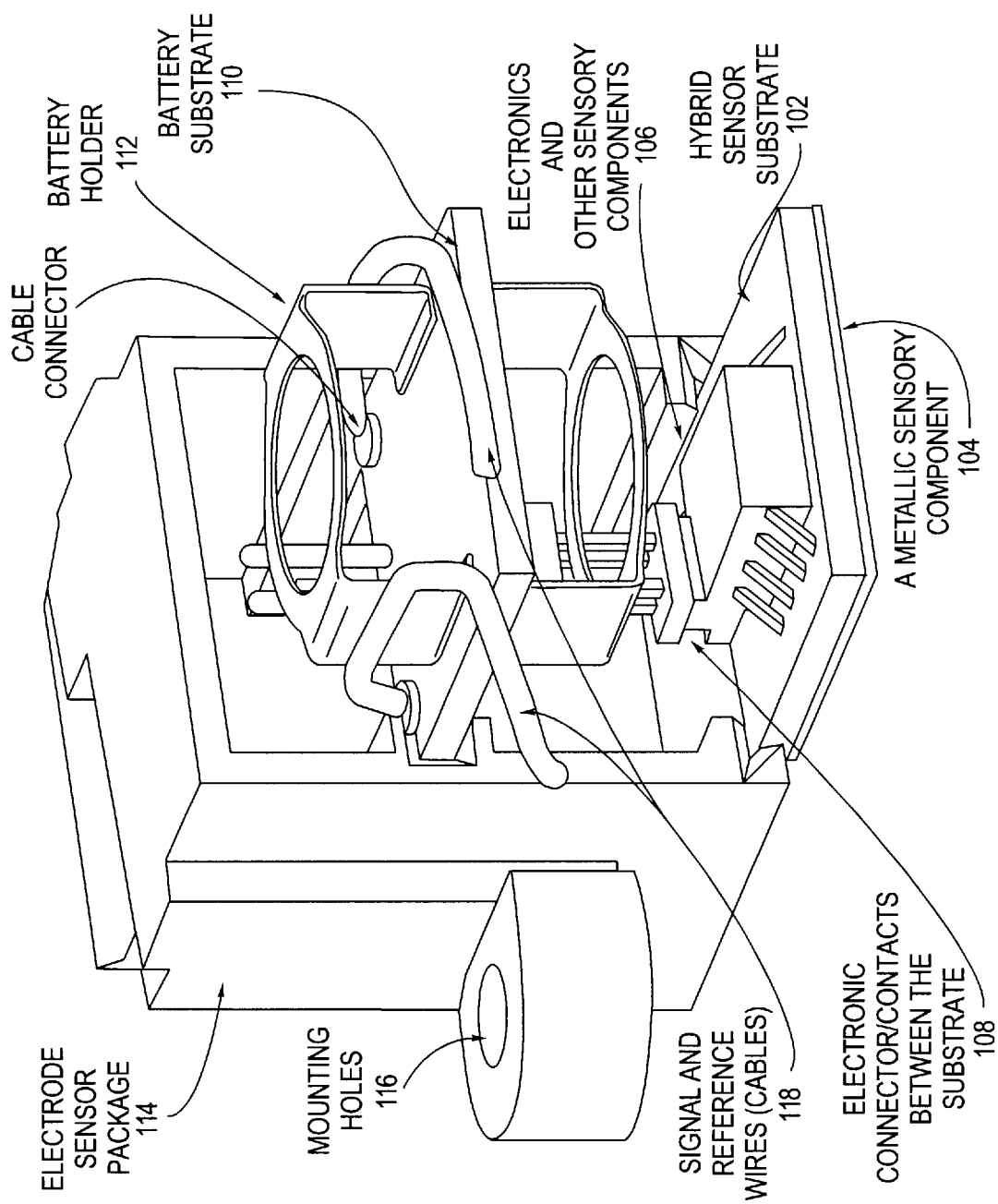
FIG. 1 is a hybrid sensor electrode of an embodiment.

FIG. 1 is a hybrid sensor electrode 100 of an embodiment. The hybrid sensor electrode 100 is a hybrid between dry electrodes and insulated electrodes and, unlike any of the typical dry or insulated electrodes, the hybrid sensor electrode houses the power source within the same package. This configuration minimizes interference noise, provides plug compatibility to the current monitoring systems, and reduces the possibility of accidental shocks that could arise from the monitoring system. This configuration also provides an improved signal to noise ratio (SNR), and allows for programmable signal gains of greater than two orders of magnitude using the active electronics integrated into the sensor electrode. Furthermore, the hybrid sensor electrode is scalable, wherein multiple sensing sites can be integrated onto a single substrate for built-in redundancy and performance as described herein.

The hybrid sensor electrode 100 includes, but is not limited to, a hybrid sensor substrate 102, a metallic sensory component 104 coupled between the skin, or sensing environment, and one side of the hybrid sensor substrate 102, sensory components and electronics 106 coupled to another side of the hybrid sensor substrate 102, an electronic connector/connection 108 to a battery substrate 110 housing one or two battery holders 112, and a package or housing 114. The housing 114 may be attached to a strap using mounting holes 116 or to the surface of the skin using adhesive tape. A wire or cable 118 transfers signals between the hybrid sensor electrode 100 and external instrumentation, but the embodiment is not so limited. While an embodiment uses batteries as a power source, solar cells or other power sources may be used.

Figure 2:
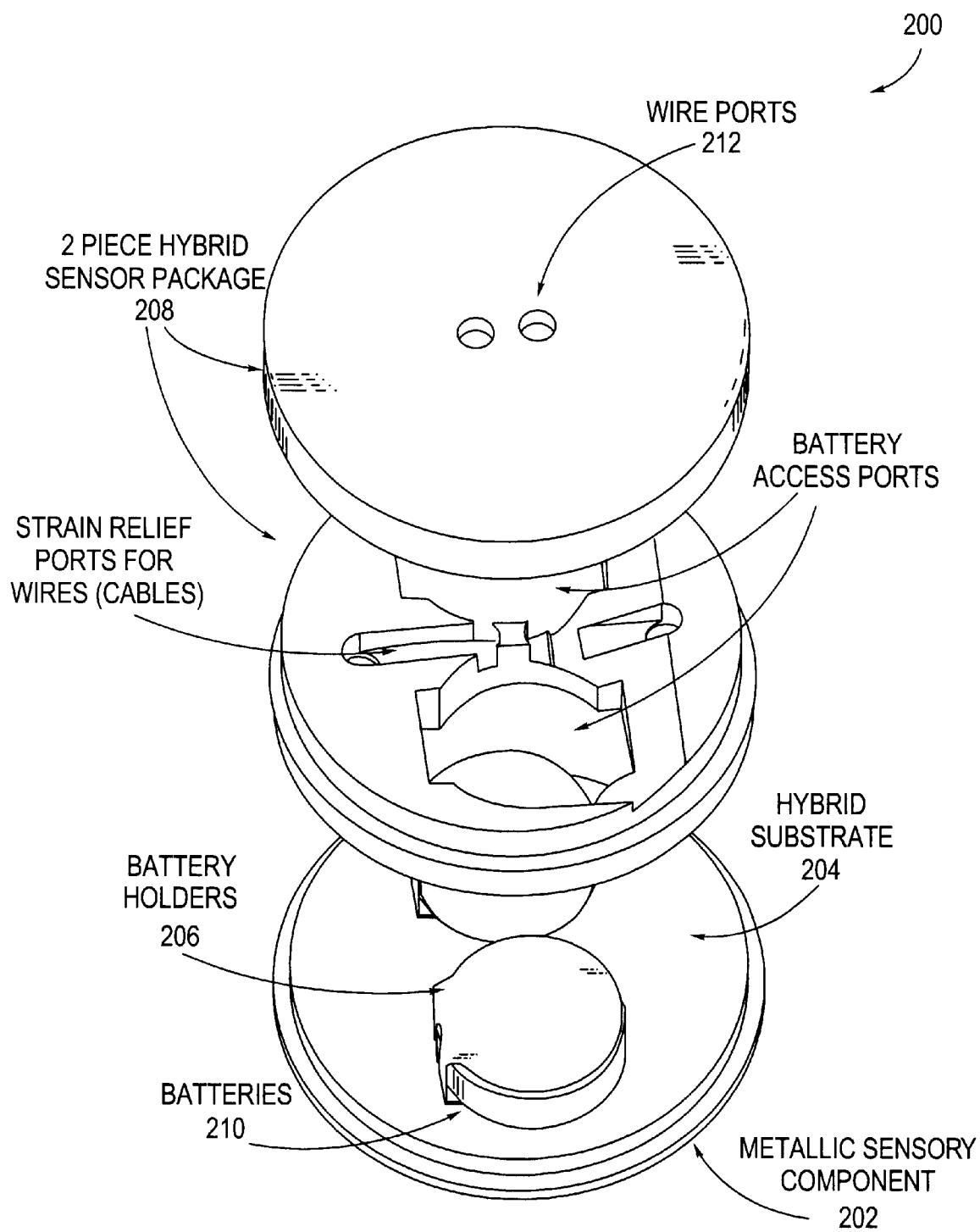
FIG. 2 is the hybrid sensor electrode an alternate embodiment.

FIG. 2 is a hybrid sensor electrode 200 of an alternate embodiment. This hybrid sensor electrode includes, but is not limited to, a metallic sensory component 202 coupled between the sensing environment and one side of a hybrid sensor substrate 204, sensory components and electronics coupled to another side of the hybrid sensor substrate, an electronic connector/connection to a battery substrate housing battery holders 206, and a two-piece package 208. The metallic sensory component 202 includes a smooth flat surface for contact with the skin, but is not so limited. The package 208 includes a hybrid sensor housing and a housing cap, both removeably coupled to the hybrid sensor substrate. The package 208 may be attached to a strap using mounting holes or to the surface of the skin using adhesive tape. A wire or cable coupled through the wire ports 212 transfers signals between the hybrid sensor electrode 200 and external instrumentation, but the embodiment is not so limited. While an embodiment uses batteries 210 as a power source, solar cells or other power sources may be used. Furthermore, while an embodiment uses a permanent metallic sensory component, a disposable metallic sensory component may be used.

Figure 3:
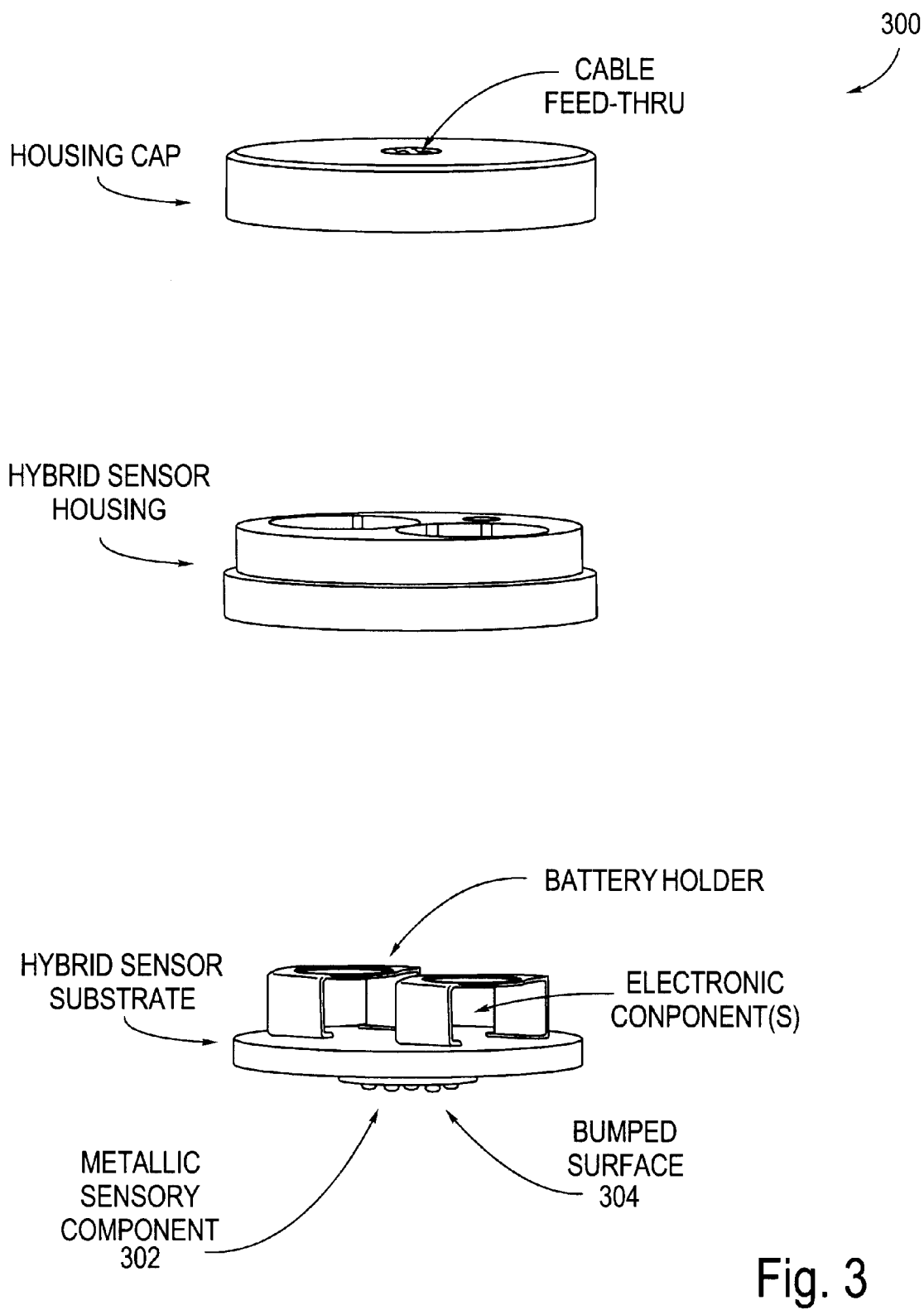
FIG. 3 is a hybrid sensor electrode of another alternate embodiment.

FIG. 3 is a side view of a hybrid sensor electrode 300 of another alternate embodiment. This alternate hybrid sensor electrode 300 includes a metallic sensory component 302 having a rough or bumped surface 304. This rough surface 304 provides for contact with the skin over hair, for example on the scalp, and can be a disposable component.

Figure 4:
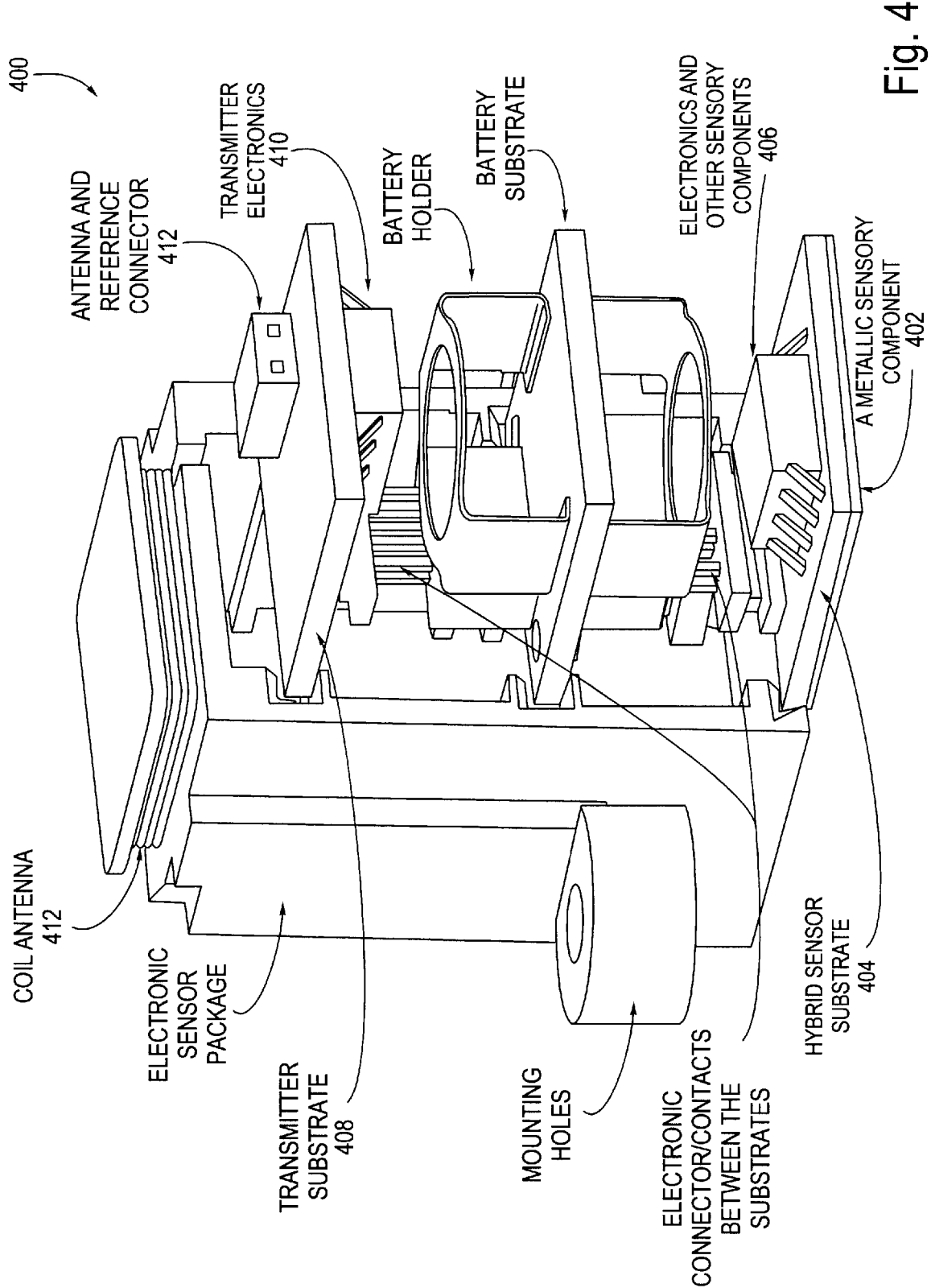
FIG. 4 is a wireless hybrid sensor electrode of an embodiment.

FIG. 4 is a wireless hybrid sensor electrode 400 of an embodiment. The wireless hybrid sensor electrode 400 includes, but is not limited to, a metallic sensory component 402 coupled to a hybrid sensor substrate 404 housing sensory electronics and components 406. Wireless technology is integrated into the sensor package using a transmitter substrate 408, transmitter electronics 410, and antenna components 412 to enable the telemetering of both data and power.

Figure 5:
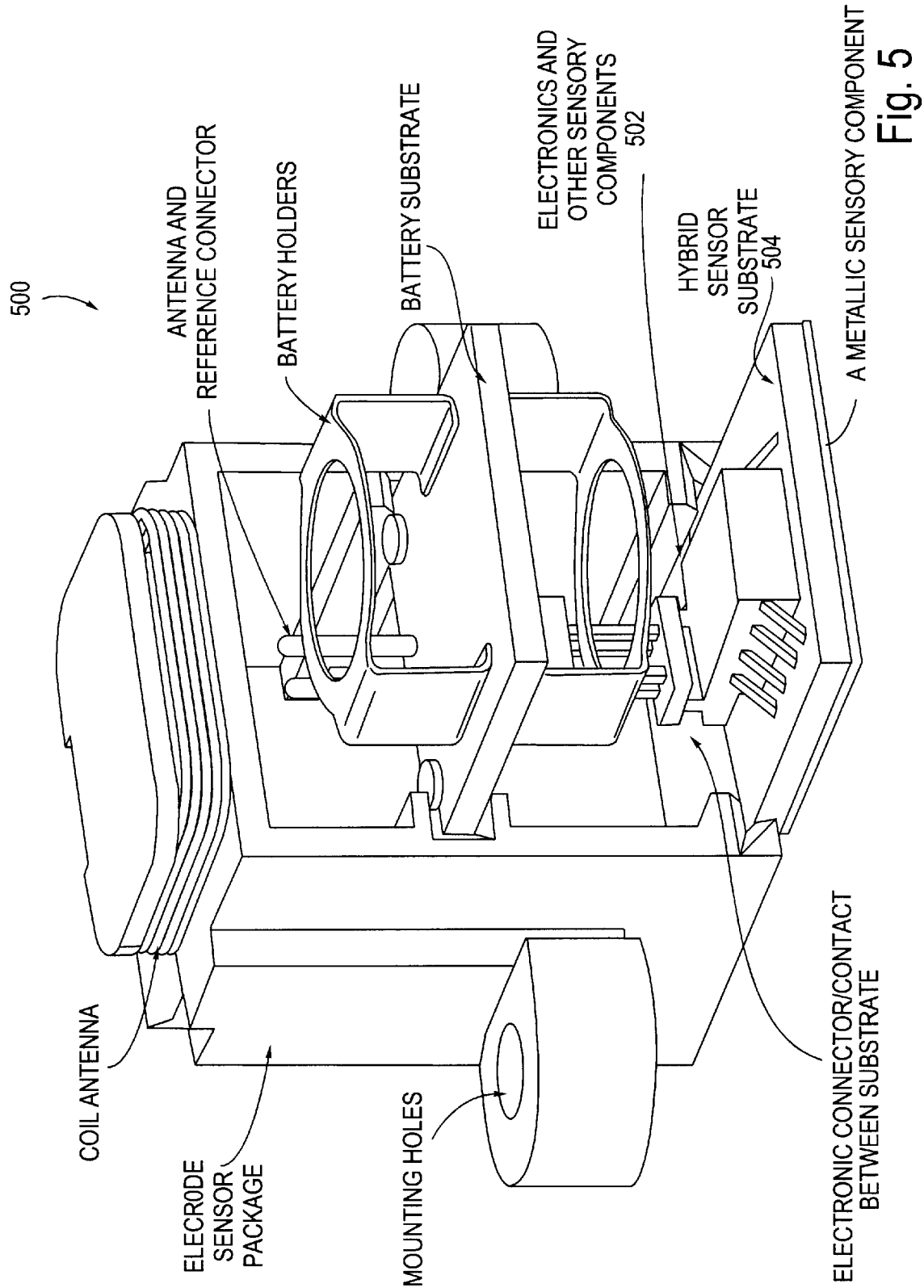
FIG. 5 is a wireless hybrid sensor electrode of an alternate embodiment.

FIG. 5 is a wireless hybrid sensor electrode 500 of an alternate embodiment. While the wireless hybrid sensor electrode 400 of FIG. 4 includes a separate transmitter substrate 408 housing the transmitter electronics 410 and the antenna/reference signal connector 412, the alternate embodiment 500 has the components of the transmitter 502 on the electrode holder substrate 504 and eliminates the transmitter substrate 408. Further alternative embodiments of the wireless hybrid sensor electrode described herein utilize radio frequency (RF) powering to remotely provide power to the sensor electronics, thereby eliminating the batteries as a power source.

A hybrid sensor electrode package or housing of an embodiment comprises a main housing and a cover piece. The cover piece locks into the main housing, but is not so limited. A windowed hybrid sensor electrode package exposes a metallic sensory component on one side of the substrate to the environment, and isolates other components from the environment. The package integrates the conditioning circuitry and battery substrate with strap mounting holes. The power source of this embodiment includes batteries that are held in place by holders on a separate substrate and connected electrically to the sensor substrate.

An alternate embodiment of the hybrid sensor electrode package includes a package type comprising a single piece housing. The single piece housing allows for a disposable version of the hybrid sensor electrode by providing a housing that snap connects to a disposable sensor substrate. The disposable version eliminates battery or sensor replacement.

FIG. 6 is a functional block diagram of a hybrid sensor electrode 600 of an embodiment. The hybrid sensor electrode 600 includes an interface 602 that receives signals from a sensor pick-up section 604 and provides signals to monitoring/controlling instruments 606. The interface 602 can be coupled to the monitoring/controlling instruments 606 using cables or using a wireless interface, but is not so limited. The interface 602 is coupled to sensory circuitry including stimulation circuitry 608, or sensor stimuli circuitry, sensory components 610, and conditioning circuitry 604, or sensor pick-up circuitry. The stimulation circuitry 608 and the conditioning circuitry 604 are coupled to a sensory component 610 that receives signals or data from the environment 612 that is being monitored. The monitored environment 612 includes but is not limited to human skin and animal skin. A power source 614 is coupled to each of the interface 602, stimulation circuitry 608, sensory component 610, and conditioning circuitry 604.

The interface 602 of an embodiment can be analog or digital. Using an analog interface, the interface block includes a conductive wire and amplifier. Using a digital interface, the interface block comprises several components including analog-to-digital (A/D) converters, memory, and a digital input/output interface.

FIG. 7 is a functional block diagram of a hybrid sensor electrode digital interface 700 of an embodiment. The digital interface 700 includes at least one analog-to-digital (A/D) converter 708, memory 710, protocol input/output (I/O) interface units 702, and a state machine 706, but is not so limited. The interface 700 can be realized using low power circuitry comprising complementary metal-oxide semiconductor (CMOS) circuitry or SiGe/CMOS process circuitry, but is not so limited.

The I/O interface unit 702 communicates with the monitoring and controlling instrumentation 704 using a custom digital protocol. The state machine 706, as the controller for the digital interface 700, monitors and sequences the A/D converter 708, memory 710, and interface units 702. The state machine 706 can partially reside in the memory 710, but is not so limited.

The A/D converter 708 includes a 12-bit A/D realized in complementary metal-oxide semiconductor (CMOS) technology with a low power design using successive approximation or delta-sigma modulation techniques, but is not so limited. The A/D converter 708 receives input from the analog sensor section and converts the signal to a 12 bit or larger bit digital word.

The memory device or memory 710 is used to store manufacturing data, and as a data buffer to the interface 700 and the instrument. The memory device 710 includes memory selected from a group including electrically erasable programmable read only memory (EEPROM), flash memory, or other types of non volatile memory. The memory device 710 may be integrated with or separated from the A/D converter circuitry 708.

Figure 8:
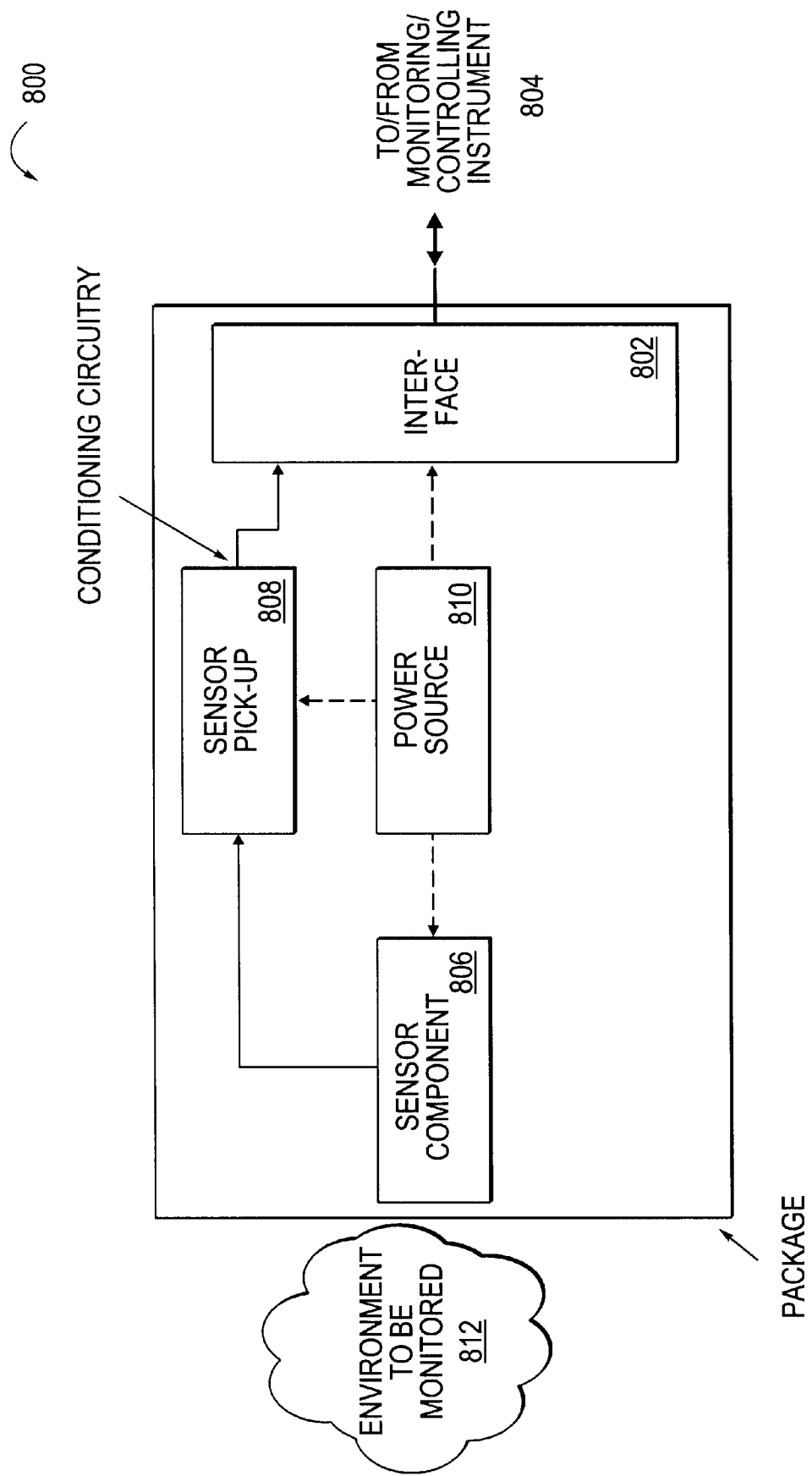
FIG. 8 is a functional block diagram of a hybrid sensor electrode of an alternate embodiment.

FIG. 8 is a functional block diagram of a hybrid sensor electrode 800 of an alternate embodiment. In this alternate embodiment, the hybrid sensor electrode 800 includes an interface 802 that receives signals from and provides signals to monitoring/controlling instruments 804. The interface 802 is coupled to sensory circuitry including sensory components 806 and conditioning circuitry 808, or sensor pick-up circuitry. The interface 802 couples biopotential signals received from the monitored environment 812 by the sensory component 806 through the conditioning circuitry 808 to the monitoring/controlling instruments or external instrumentation 804. A power source 810 is coupled to each of the interface 802, sensory component 806, and conditioning circuitry 808.

Figure 9:
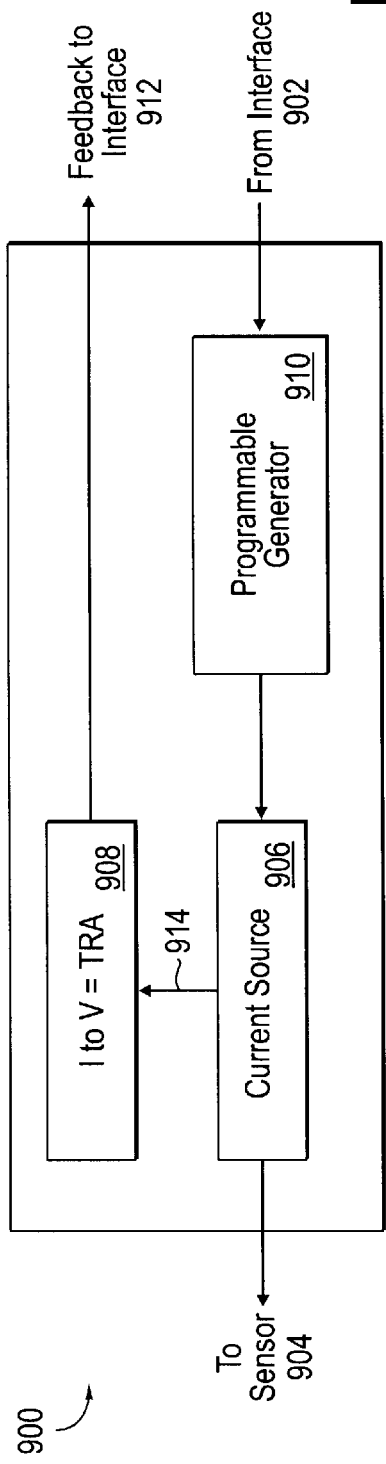
FIG. 9 is a block diagram of stimulation circuitry of a hybrid sensor electrode of an embodiment.

FIG. 9 is a block diagram of stimulation circuitry 900 of a hybrid sensor electrode of an embodiment. The stimulation circuitry 900 is coupled to transfer signals between the interface 902 and the sensory component 904. The stimulation circuitry 900 includes, but is not limited to, voltage/current (V/I) source circuitry 906, current-to-voltage converter or transresistance (TRA) amplifier 908, and programmable generator circuitry 910. The programmable generator 910 is coupled between the interface 902 and the current source 906. The current source 906 is coupled to the sensor 904 and the TRA 908. The current source output 914 can be dynamically monitored by the TRA 908 in order to operate in a closed-loop control fashion for accuracy and reliability. The TRA output is coupled as feedback 912 to the interface.

Figure 10:
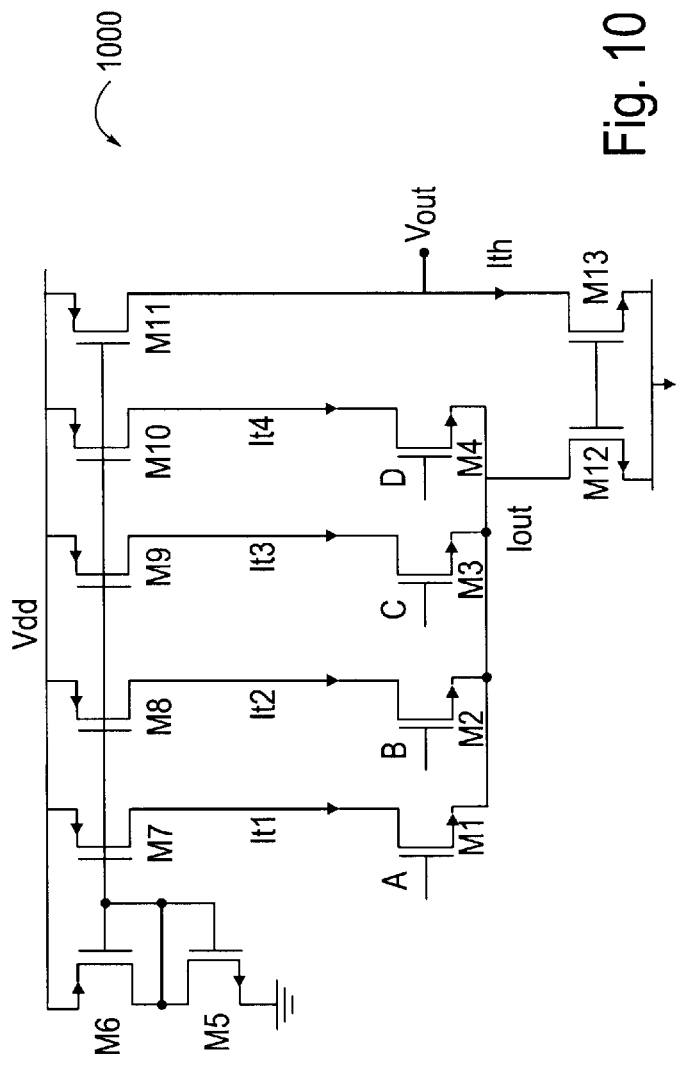
FIG. 10 is a schematic diagram of stimulation circuitry of a hybrid sensor electrode of an embodiment.

FIG. 10 is a schematic diagram of stimulation circuitry 1000 of a hybrid sensor electrode of an embodiment. An embodiment of the circuitry uses CMOS technology, but is not so limited. The programmable current source includes transistors M5 and M6 as references and transistors M7 to M10 as current mirrors that establish a current threshold for transistors M1 to M4. The signal inputs to transistors M1 to M4 are labeled as A,B,C,D respectively. These input signals are used to add or turn off the respective transistors for summing current at the node labeled Iout. The transistors M11, M12, and M13 form the TRA that converts the summed current to a voltage if a threshold (Ith) is exceeded, feeding back to the interface to turn off one or several of the M1 to M4 devices for lower current output. A portion of the Iout current is delivered to the skin of a subject. The delivered current should not exceed 100 micro amps and it can be as low as 5 micro amps.

Figure 11:
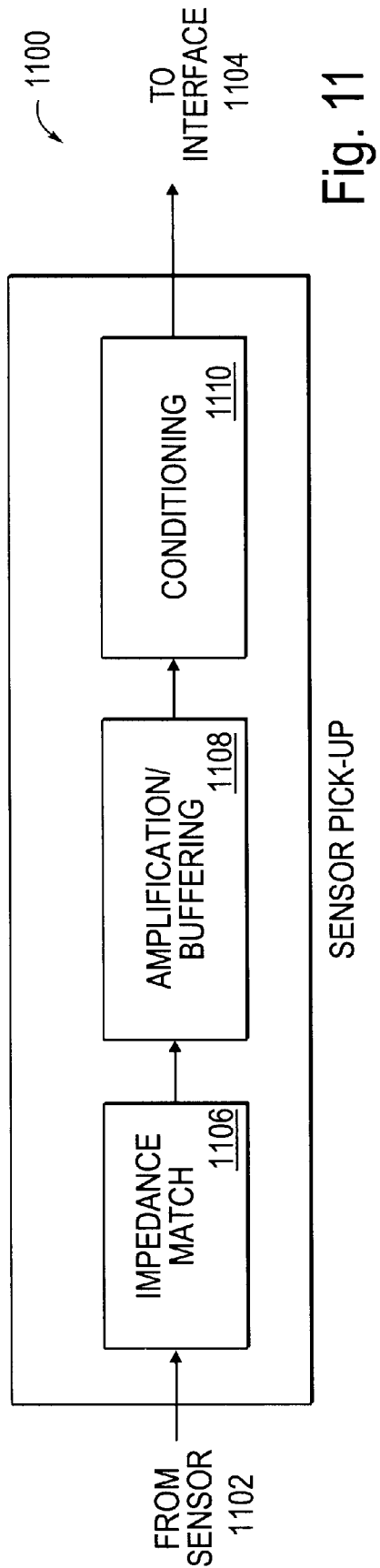
FIG. 11 is a block diagram of sensor pick-up circuitry of a hybrid sensor electrode of an embodiment.

FIG. 11 is a block diagram of sensor pick-up circuitry 1100 of a hybrid sensor electrode of an embodiment. The sensor pick-up circuitry 1100, or conditioning circuitry, is coupled to transfer signals between the sensory component 1102 and the interface 1104. The sensor pick-up circuitry 1100 includes, but is not limited to, impedance matching circuitry 1106, amplification/buffering circuitry 1108, and conditioning circuitry 1110. The impedance matching circuitry 1106 provides charge balancing for the sensing element, impedance matching to minimize loading with a feedback controlled amplifier that has low noise and low offset characteristics. The amplification and buffering circuitry 1108 provides programmable gain control, a programmable filter for frequency band selection, and feedback control for minimization of noise and drift. The conditiong circuitry 1110 provides signal level shifters, output electronic static discharge protection, and input/output matching.

Figure 12:
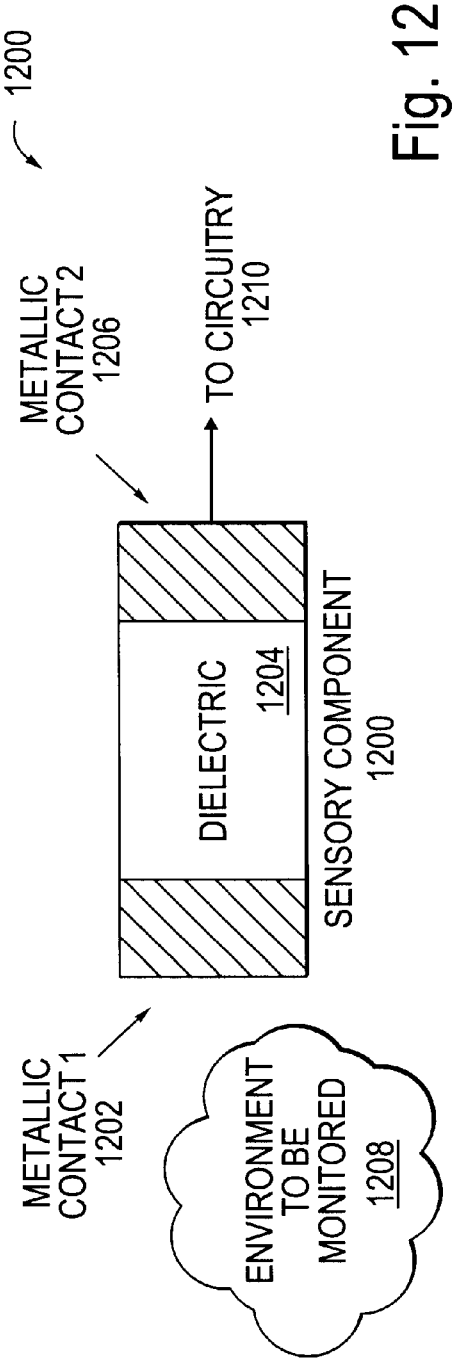
FIG. 12 is a sensory element of a hybrid sensor electrode of an embodiment.

FIG. 12 is a sensory element 1200 of a hybrid sensor electrode of an embodiment. The sensory element 1200 includes a first metallic contact 1202 coupled to a first side of a dielectric 1204 and a second metallic contact 1206 coupled to a second side of the dielectric 1204. The first metallic contact 1202 is placed in the environment 1208 to be monitored. The second metallic contact 1206 is coupled to other sensory elements and circuitry 1210.

The hybrid sensory element of an embodiment is a hybrid between dry electrodes and insulated electrodes as it provides metallic contact at both ends and allows means of stimulating the sensor environment in addition to sensing the signals from the environment. Like the dry electrodes, the sensor has a metallic or conductive material (e.g., Gold, Stainless Steel) in contact with the skin. Similar to the insulated electrode, the coupling to the skin is capacitive. The capacitive coupling to the skin in an embodiment of the hybrid sensor electrode is via a metallic contact with the skin followed by a dielectric, a metallic material followed by a dissimilar metallic material, then transimpedance amplifiers and circuits for signal conditioning.

Figure 13:
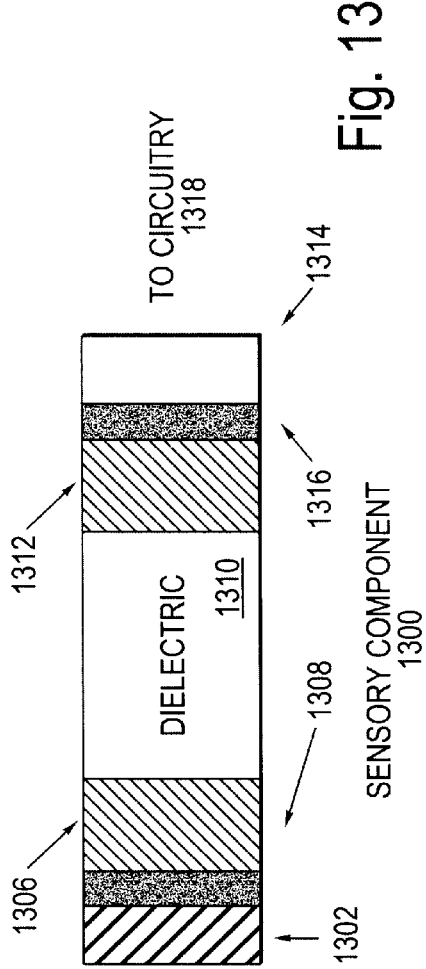
FIG. 13 is an alternate sensory element or component of a hybrid sensor electrode of an embodiment.

FIG. 13 is an alternate sensory element or component 1300 of a hybrid sensor electrode of an embodiment. The sensory element 1300 includes a first metallic contact 1302 coupled to the environment to be sensed 1304. The first metallic contact 1302 is also coupled to a second metallic contact 1306 via a bond 1308. The bond 1308 includes, but is not limited to, a metallic bond, a metallic snap connector, and any other type of metallic contact that electrically couples the first metallic contact 1302 to the second metallic contact 1306 such that the first metallic contact 1302 is removable and disposable. The second metallic contact 1306 is coupled to one side of a dielectric 1310. Another side of the dielectric 1310 is coupled to a third metallic contact 1312. The third metallic contact 1312 is coupled to a fourth metallic contact 1314 via another bond 1316. The fourth metallic contact 1314 couples to the hybrid sensor electrode circuitry 1318 and other sensory elements.

Figure 14:
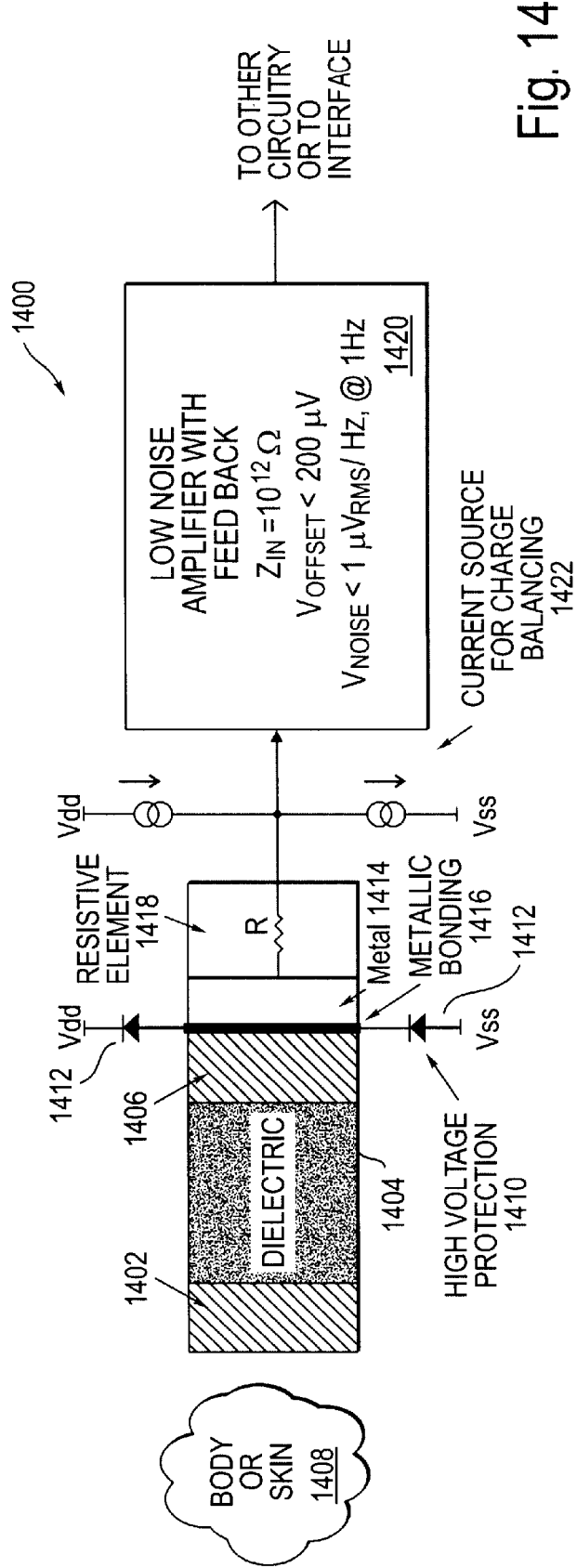
FIG. 14 is a sensory element configuration of a hybrid sensor electrode of an embodiment.

FIG. 14 is a sensory element configuration 1400 of a hybrid sensor electrode of an embodiment. This sensory element configuration 1400 can be used with any of the sensor elements described herein, but is not so limited. The sensory element 1400 includes a first metallic contact 1402 coupled to a first side of a dielectric 1404 and a second metallic contact 1406 coupled to a second side of the dielectric 1404. The first metallic contact 1402 is placed in the environment to be monitored 1408. The second metallic contact 1406 is coupled to protection circuitry 1410. The protection circuitry 1410 includes back-to-back diodes 1412 for high voltage protection, but is not so limited. The second metallic contact 1406 is coupled to a resistive element 1418 using a third metallic contact 1414 and a metallic bond 1416. The resistive element 1418 is coupled to a low noise amplifier 1420 through a charge balancing current source/sink 1422. The low noise amplifier 1420 includes feedback, but is not so limited.

Regarding transduction/sensing mechanisms, the sensory element of an embodiment, when in contact with the surface of the body or the skin, or in close proximity to the environment of the surface of the body, forms a completed network that allows biopotentials (e.g., ionic) or fields to be picked up from the surface of the skin and transferred to instruments for analysis and recording. The functioning of the sensor can be described as a network of electrical circuit components such as amplifiers, resistors, capacitors and impedances. The sensor, when in contact with the skin, provides a means of converting the ionic potential at the skin boundary to electrical potentials. When in the vicinity of the skin, the sensor converts the electrical field near the skin to electrical potential. Consequently, the sensor serves as two integrated sensors that convert both ionic potentials and electric fields to electrical potential such that it can be monitored and recorded by instruments to which it is coupled. The sensor output provides the electrical interface for utilizing four types of biopotential signals and for connecting to the associated electrocardiogram (EKG), electroencephalogram (EEG), electromyogram (EMG), and electro-oculogram (EOG) instrumentation without additional conditioning.

In the design of the hybrid sensor electrode of an embodiment, the effects of changing skin impedance are minimized by introducing an electrode input impedance placed in series with the skin impedance that has a much larger magnitude (electrode-dominant impedance). This electrode input impedance includes a sensor impedance in series with the skin impedance coupled to the local amplifier input impedance and charge balancing circuitry. The local amplifier circuitry of an embodiment should have a very high input impedance (greater than 1 terra ohm), low offset voltage (less than 200 microvolts), low noise (less than 1 microvolt root mean square (rms) per root hertz (Hz) at 1 Hz) and operate at voltages less than 3 volts (V). The charge balancing circuitry should be able to leak or provide current to the amplifier and sensory element node currents as low as 10 nano amperes and as high as 1 micro amperes. The charge balancing circuitry minimizes direct current (DC) offset and motion artifacts caused by the motion of the subject and variation of low frequency components of the biopotential.

Figure 15:
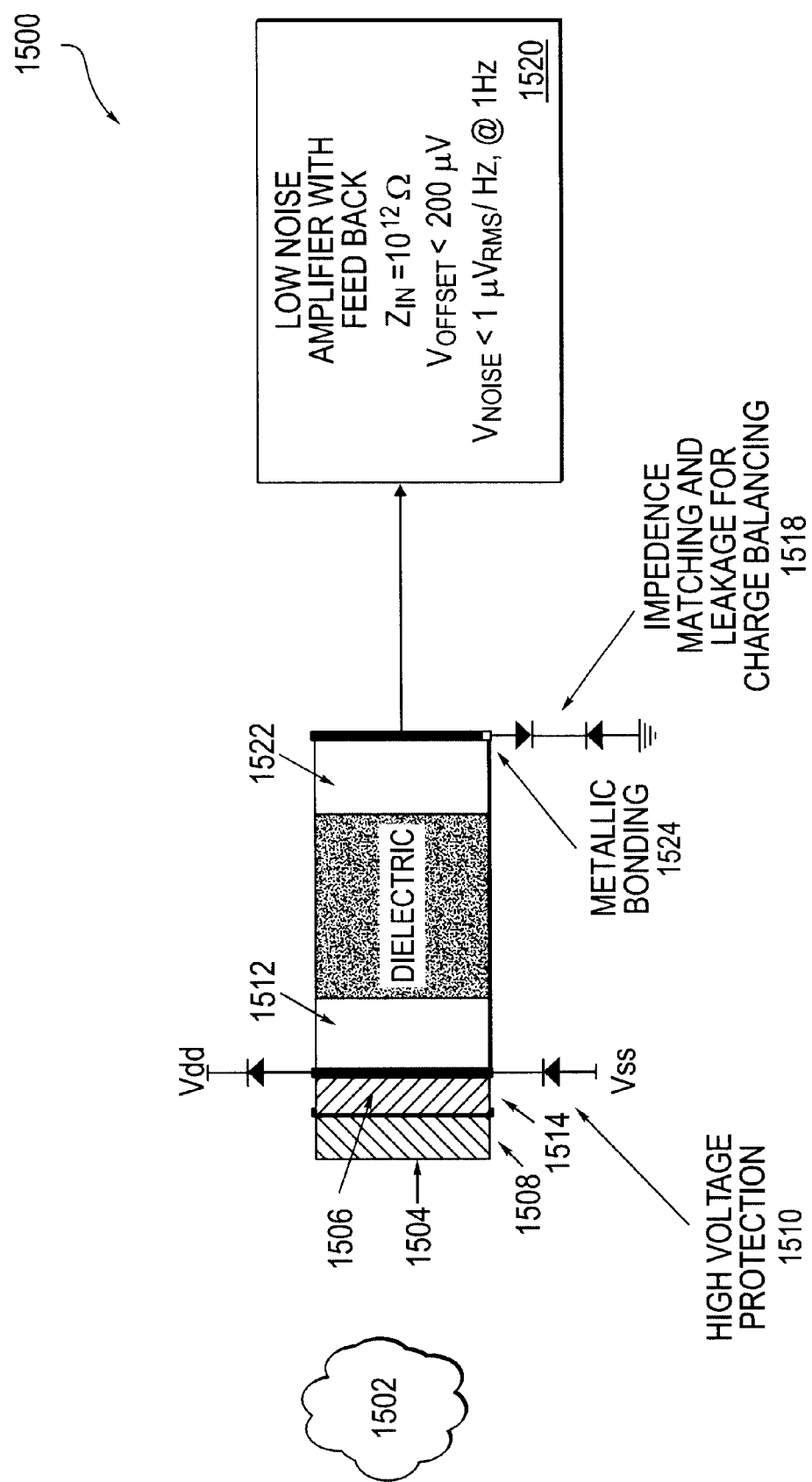
FIG. 15 is an alternate sensory element configuration of a hybrid sensor electrode of an embodiment.

FIG. 15 is an alternate sensory element configuration 1500 of a hybrid sensor electrode of an embodiment. This sensory element configuration 1500 can be used with any of the sensor elements described herein, but is not so limited. The sensory element 1500 includes a first metallic contact 1504, placed in the environment to be monitored 1502, coupled to a second metallic contact 1506 using a metallic bond 1508. The second metallic contact 1506 is coupled to protection circuitry 1510, for example back-to-back diodes. The second metallic contact 1506 is coupled to a third metallic contact 1512 using a metallic bond 1514. The third metallic contact 1512 is coupled to a side of a dielectric 1516. Another side of the dielectric 1516 is coupled to common cathode diode circuitry 1518 and the input of a low noise amplifier 1520 using a fourth metallic contact 1522 and a metallic bond 1524.

The effects of changing skin impedance are minimized in the hybrid sensor electrode by introducing an electrode input impedance placed in series with the skin impedance. The electrode input impedance includes a sensor impedance in series with the skin impedance coupled to the local amplifier input impedance and charge balancing circuitry. The local amplifier circuitry of an embodiment has a very high input impedance (equal to or greater than 1 terra ohm), low offset voltage (less than 200 microvolts), low noise (less than 1 microvolt rms per root hertz at 1 Hz) and operates at voltages less than 3 volts. The charge balancing circuitry of an embodiment leaks or provides current to the amplifier and sensory element node approximately in the range 10 nano amperes to 1 micro amperes. The charge balancing minimizes DC offset and motion artifacts caused by the motion of the subject and variation of low frequency components of the biopotential at the skin. In this embodiment, the charge balancing circuitry comprises a common cathode diode that further serves as protection against high voltages, and provides large input impedance.

Regarding the selection of electrode materials, a number of materials have been investigated for thin-film capacitor fabrication, where some of the commonly used materials include silicon monoxide (SiO), silicon dioxide ($SiO_2$), silicon nitride ($Si_3N_4$), Diamond like Carbon (DLC), and tantalum pentoxide ($Ta_2O_5$). Tantalum pentoxide is used as the dielectric material of an electrode of an embodiment.

The properties of the dielectric material of an embodiment of the electrode include, but are not limited to: low reaction with sodium chloride (NaCl) for biocompatibility and sensor protection; low deposition temperature (less than 500 degrees Celsius) to be compatible with the electrode material (the melting point of aluminum is 660 degrees Celsius); high dielectric constant for obtaining a large capacitance in a small area; high dielectric strength (needing high breakdown voltage, or BV) for electrostatic protection; and, moderate leakage resistance for impedance matching to the amplifier. Considering these factors, silicon nitride ($Si_3N_4$) is used as the dielectric material of an embodiment. Silicon nitride is an extremely good barrier to the diffusion of water and ions, particularly sodium ($Na^+$) ions. Furthermore, silicon nitride oxidizes 30 times slower than silicon, adheres well to aluminum, and has a high dielectric constant. Moreover, silicon nitride can be deposited by plasma-enhanced chemical vapor deposition (PECVD), atmospheric-pressure chemical vapor deposition (APCVD), and low pressure chemical vapor deposition (LPCVD), with each of these deposition techniques resulting in different nitride characteristics. Following selection of the dielectric, electrode, and substrate materials, dielectric film deposition conditions and thickness are optimized.

Figure 16:
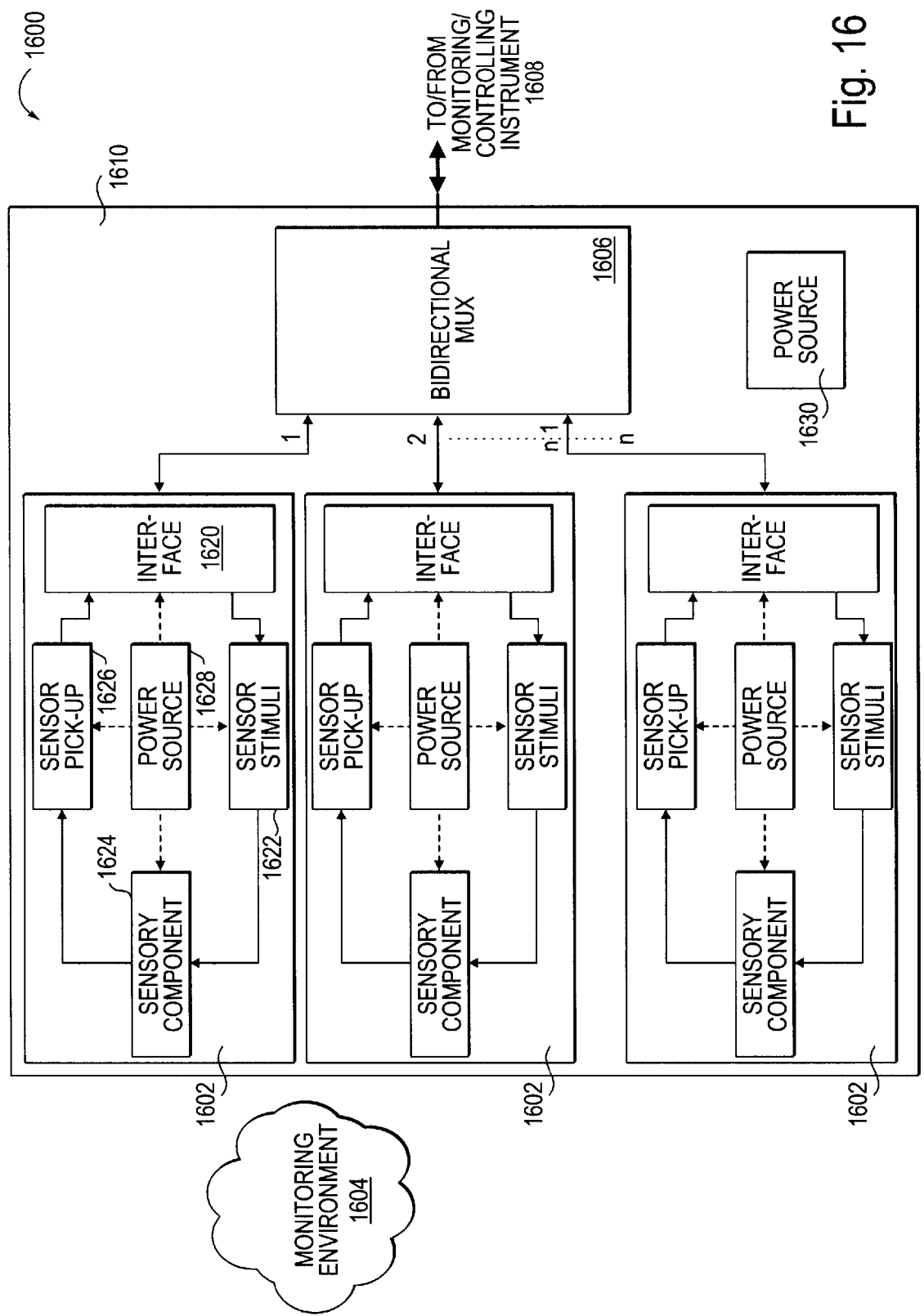
FIG. 16 is a functional block diagram of a hybrid sensor electrode array of an embodiment.

The hybrid sensor electrode of an embodiment is scalable, and this allows for the integration of multiple sensing sites onto a single substrate for built-in redundancy and performance. FIG. 16 is a functional block diagram of a hybrid sensor electrode array 1600 of an embodiment. The array 1600 includes a number of hybrid sensor electrodes 1602 on a single substrate 1610, where the electrodes are coupled to the monitored environment 1604, but is not so limited. The monitored environment 1604 includes but is not limited to human skin and animal skin. The electrodes 1602 are coupled to a bidirectional multiplexer 1606 that provides for communications among the hybrid sensor electrodes 1602 and monitoring/controlling equipment or external instrumentation 1608.

The hybrid sensor electrode 1602 includes an interface 1620 that receives signals from and provides signals to monitoring/controlling instruments 1608 through the bidirectional multiplexer 1606. The bidirectional multiplexer 1606 can be coupled to the monitoring/controlling instruments 1608 using a wired interface, a wireless interface, or a combination wired/wireless interface, but is not so limited. The interface 1620 is coupled to sensory circuitry including stimulation circuitry 1622 or sensor stimuli circuitry, sensory components 1624, and conditioning circuitry 1626, or sensor pick-up circuitry. The interface 1620 of an embodiment couples signals from the interface 1620 through the stimulation circuitry 1622 and sensory component 1624 to the conditioning circuitry 1626 and back to the interface 1620. The stimulation circuitry 1622 and the conditioning circuitry 1626 are coupled to a sensory component 1624 that receives signals or data from the environment 1604 that is being monitored. A power source 1628 is coupled to each of the interface 1620, stimulation circuitry 1622, sensory component 1624, and conditioning circuitry 1626. In an alternate embodiment, a single power source 1630 can be used to provide power to all of the hybrid sensor electrodes 1602 of the hybrid sensor electrode array 1600.

Figure 17:
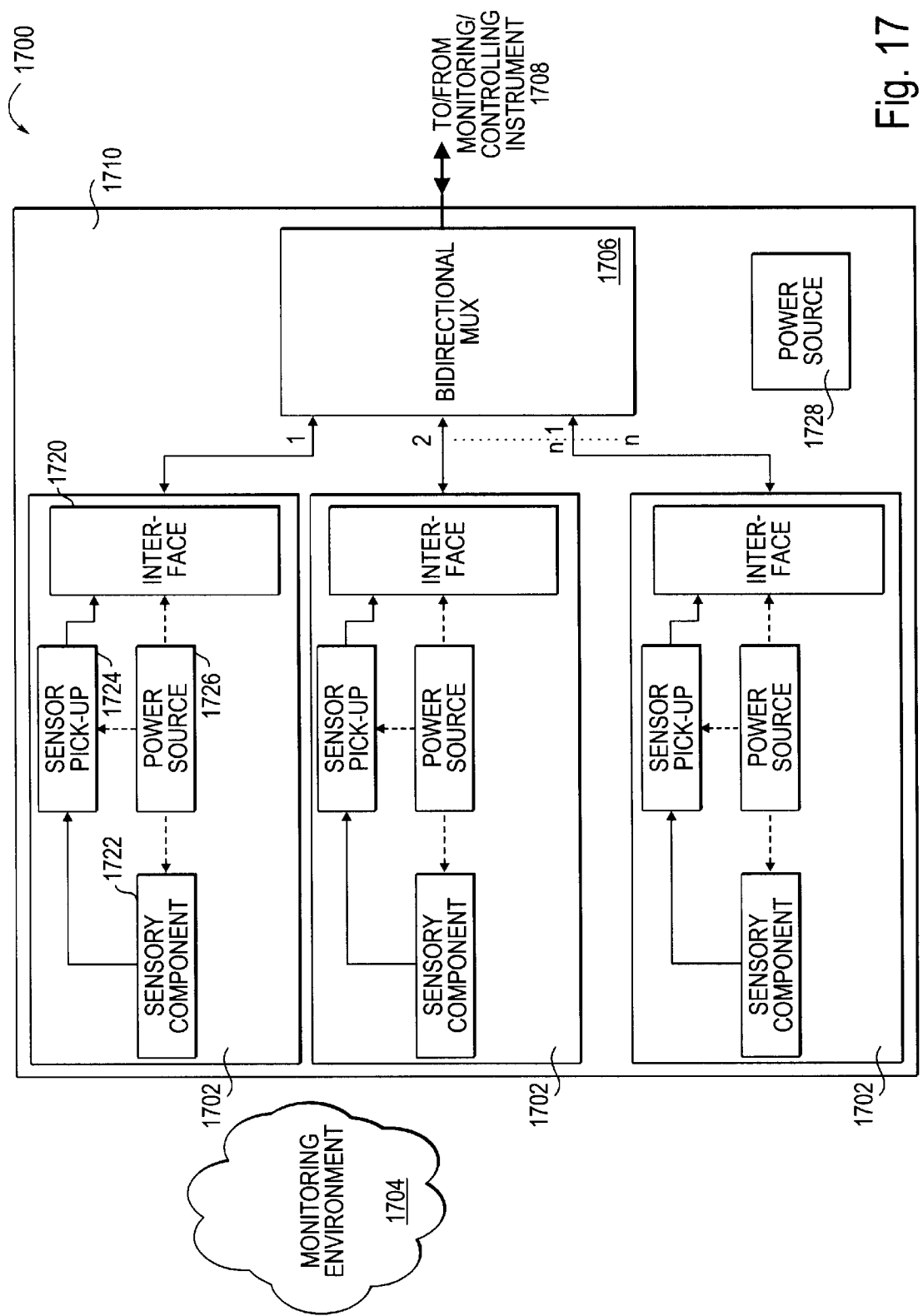
FIG. 17 is a functional block diagram of an alternate hybrid sensor electrode array of an embodiment.

FIG. 17 is a functional block diagram of an alternate hybrid sensor electrode array 1700 of an embodiment. The alternate array 1700 includes a number of alternate hybrid sensor electrodes 1702 on a single substrate 1710, where the electrodes 1702 are coupled to the monitored environment 1704, but is not so limited. The electrodes 1702 are coupled to a bidirectional multiplexer 1706 that provides for communications among the hybrid sensor electrodes 1702 and monitoring/controlling equipment 1708. The alternate hybrid sensor electrode 1702 includes an interface 1720 that receives signals from and provides signals to monitoring/controlling instruments 1708 through the bidirectional multiplexer 1706. The interface 1720 is coupled to sensory circuitry including sensory components 1722 and conditioning circuitry 1724, or sensor pick-up circuitry. A power source 1726 is coupled to each of the interface 1720, sensory component 1722, and conditioning circuitry 1724. In al alternate embodiment, a single power source 1728 can be used to provide power to all of the hybrid sensor electrodes 1702 of the hybrid sensor electrode array 1700.

The hybrid sensor electrode system of an embodiment provides a micro-telemetry system that eliminates any cables or wires used to connect the electrodes of a subject to a monitoring system. As the micro-telemetry system is co-located with the electrode, and the electrode is attached to the subject, the size, weight, power consumption and bandwidth of the transmitter section are the key parameters in design of a telemetry system for electrode systems. The transmitter section of an embodiment provides, but is not limited to, long term monitoring, low bandwidth and improved SNR and power consumption, while not disturbing the normal physical processes of the subject.

Figure 18:
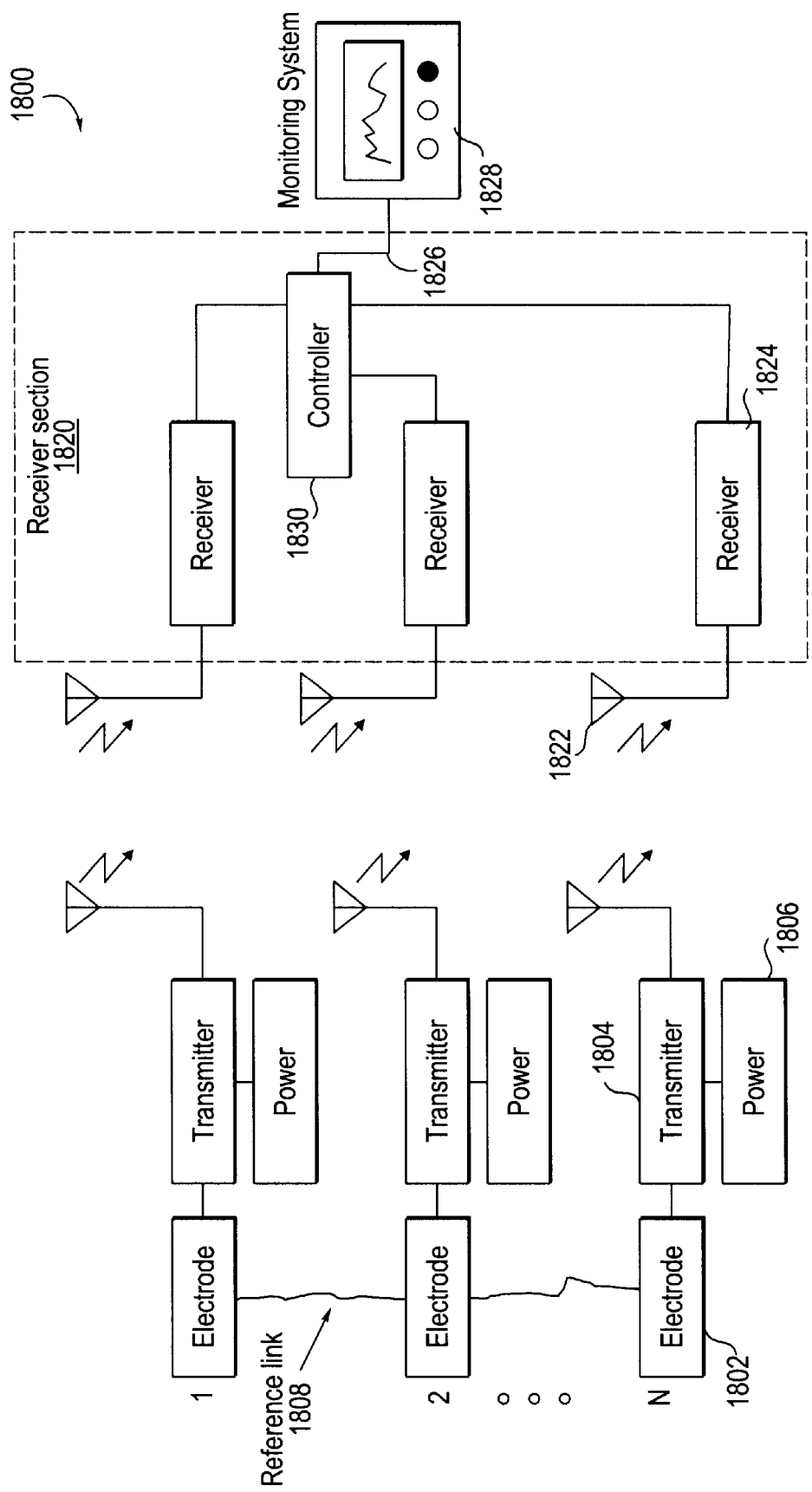
FIG. 18 is a block diagram of a telemetry system of a hybrid sensor electrode of an embodiment.

FIG. 18 is a block diagram of a telemetry system 1800 of a hybrid sensor electrode of an embodiment. Each electrode 1802 is configured with an embedded micro-transmitter 1804 and a power source 1806 that includes a battery, but is not so limited. In an alternate embodiment, the electrode 1802 and the transmitter 1804 can share the power source 1806. The transmitter 1804 is coupled to the electrode 1802 and converts the electrode signals to radio frequency signals for transmission. The transmitter 1804 has dimensions approximately in the range 5 to 20 millimeters (mm) long, 5 to 20 mm wide, and 1 to 5 mm high while weighing less than 100 milligram (mg) and using less and 100 milliwatts (mW) of discrete power, but is not so limited. As each transmitter 1804 processes signals from a single electrode 1802, the bandwidth requirement for each channel is identical, allowing for repeatable and consistent SNR. In addition, a reference link 1808 between each electrode 1802 allows all electrodes to be synchronized and referenced to a single potential. This reference link can be provided by means of current injection to the surface of the skin by a master electrode that is received by all other electrodes (slave electrodes). The reference link 1808 can also be provided using telemetry from the receiver section. Furthermore, the reference link 1808 can be provided using a wired link among the electrodes.

The receiver section 1820 of an embodiment includes up to 8 antennas 1822 and receivers 1824, wherein each receiver 1824 processes telemetry signals from numerous electrodes 1802, but is not so limited. A receiver section 1820 of an embodiment comprising up to 8 channels is modularized and expandable to convert transmitted signals from up to 256 electrodes simultaneously. The modularization allows for an increase or decrease in the number of electrodes without affecting system performance. Furthermore, each channel has adequate bandwidth for distortion free telemetry plus appropriate filtering to maximize the SNR and to prevent aliasing in sampled-data monitoring systems.

The output signal 1826 from the receiver section 1820 is compatible with and interfaces with typical electrode monitoring systems 1828. This compatibility is provided by the use of a receiver output section that is compatible in the following areas: connector plug-in to fit in standard monitoring systems; signal levels and bandwidths not exceeding the current systems requirements; and, low output impedance to prevent signal attenuation. Thus, the telemetry system of an embodiment allows for retrofit of current monitoring systems without modification. Furthermore, the receiver section 1820 can be integrated with the monitoring system 1828.

The coupling among the electrodes 1802 and the monitoring system 1828 can include a network. In an embodiment, the monitoring system can be coupled 1826 to the receiver section 1820 using network connections including wired, wireless, and combined wired and wireless connections. In an alternate embodiment, the receivers 1824 of a receiver section can be located away from the controller 1830 and coupled to the controller 1830 using network connections including wired, wireless, and combined wired and wireless connections. The controller 1830 can then be coupled 1826 to the monitoring system 1828 using network connections including wired, wireless, and combined wired and wireless connections.

Figure 19:
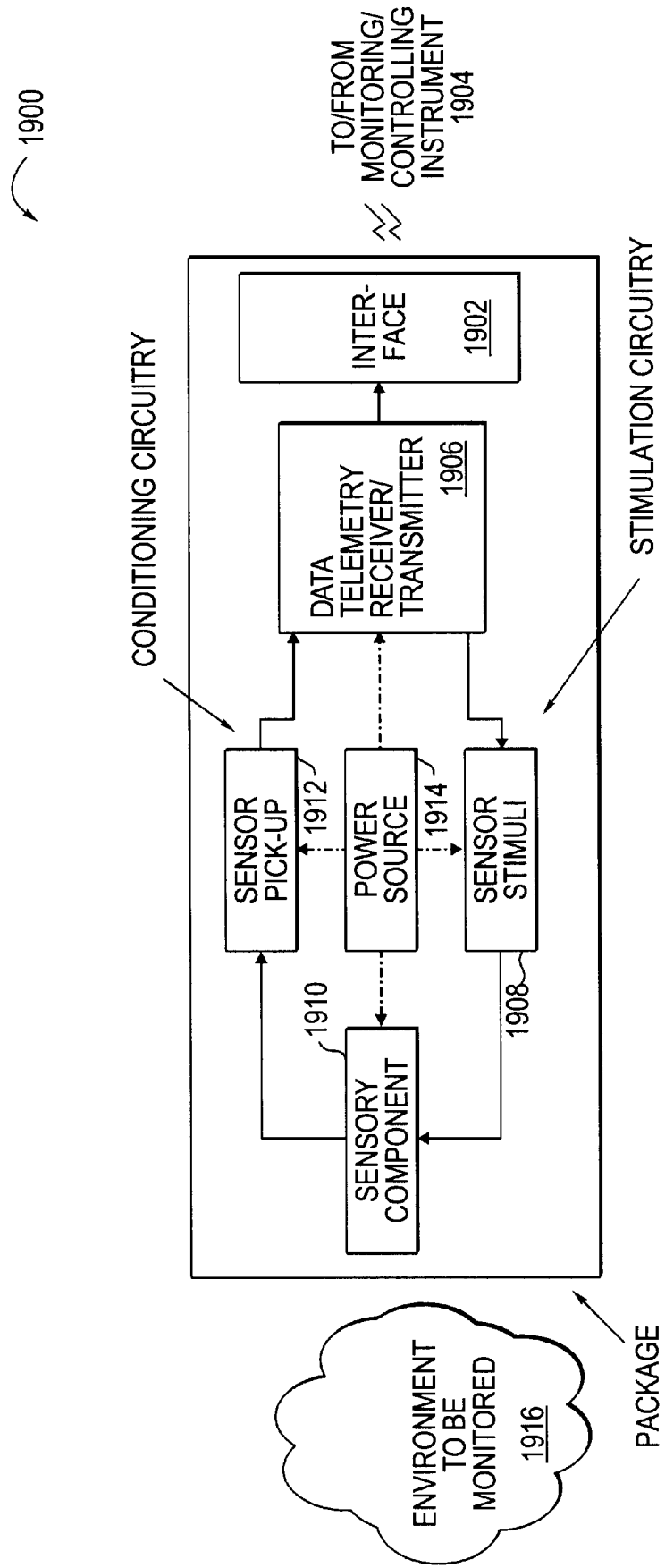
FIG. 19 is a functional block diagram of a hybrid sensor telemetry electrode of an embodiment.

FIG. 19 is a functional block diagram of a hybrid sensor telemetry electrode 1900 of an embodiment. The hybrid sensor telemetry electrode 1900 includes an interface 1902 that couples signals between circuitry of the sensor electrode and monitoring and controlling instruments 1904. The interface 1902 is coupled to the monitoring and controlling instruments 1904 using a wireless interface or network, but is not so limited. The interface 1902 is coupled to a data telemetry transmitter/receiver (transceiver) 1906 of the sensor electrode 1900, but is not so limited. In one alternate embodiment the interface 1902 can be coupled to a transmitter. In another alternate embodiment the interface can be coupled to a receiver. In yet another alternate embodiment, the interface can be separately coupled to a transmitter and a receiver.

The transceiver 1906 is coupled to sensory circuitry including stimulation circuitry 1908, or sensor stimuli circuitry, sensory components 1910, and conditioning circuitry 1912, or sensor pick-up circuitry. The stimulation circuitry 1908 and the conditioning circuitry 1912 are coupled to a sensory component 1910 that receives signals or data from the environment 1916 that is being monitored. The monitored environment 1916 includes but is not limited to human that is being monitored. The monitored environment 1916 includes but is not limited to human skin and animal skin. A power source 1914 is coupled to each of the transceiver 1906, stimulation circuitry 1908, sensory component 1910, and conditioning circuitry 1912.

Figure 20:
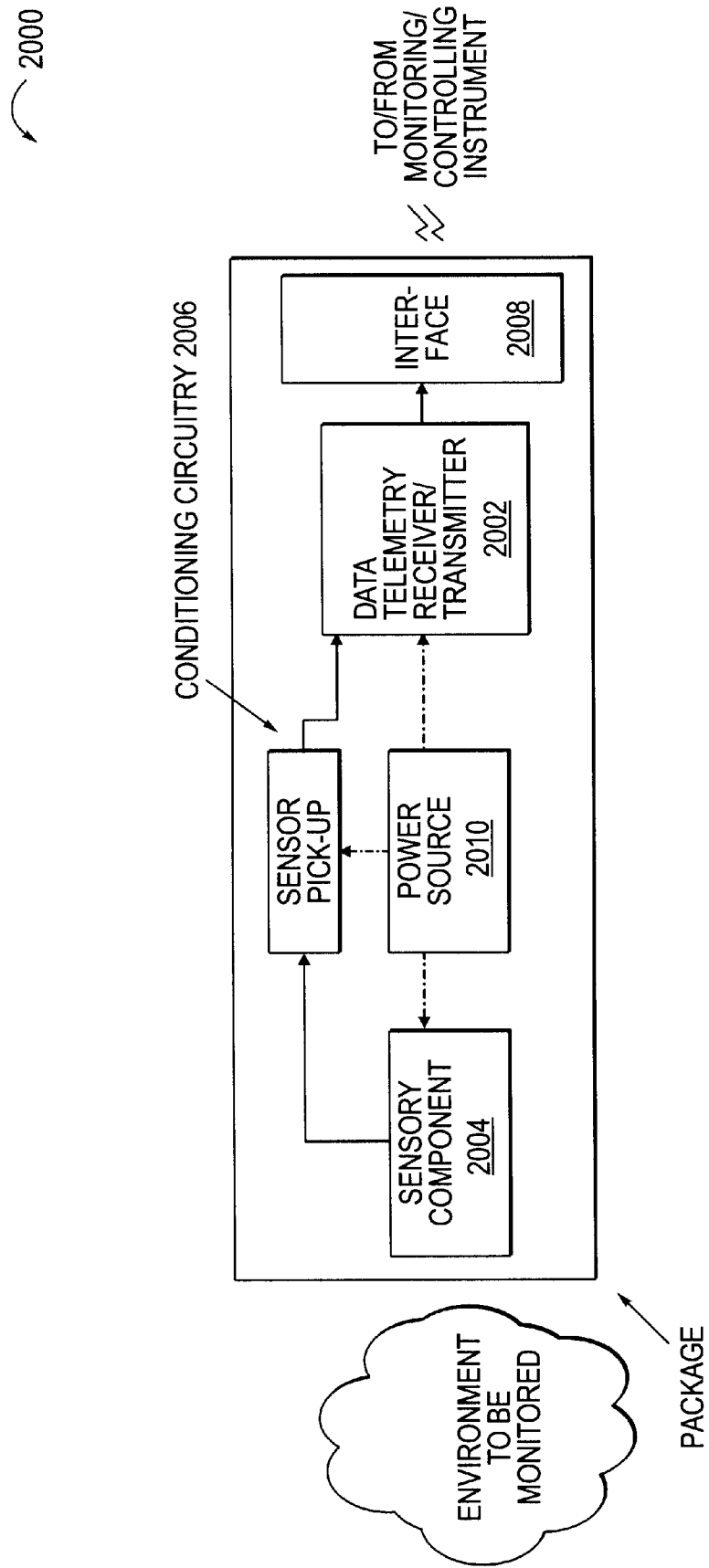
FIG. 20 is a functional block diagram of a hybrid sensor telemetry electrode of an alternate embodiment.

FIG. 20 is a functional block diagram of a hybrid sensor telemetry electrode 2000 of an alternate embodiment. In this alternate embodiment, the transceiver 2002 is coupled to sensory circuitry including sensory components 2004 and conditioning circuitry 2006, or sensor pick-up circuitry. The transceiver 2002 couples signals from the sensory component 2004 through the conditioning circuitry 2006 to the interface 2008. A power source 2010 is coupled to each of the transceiver 2002, sensory component 2004, and conditioning circuitry 2006.

Figure 21:
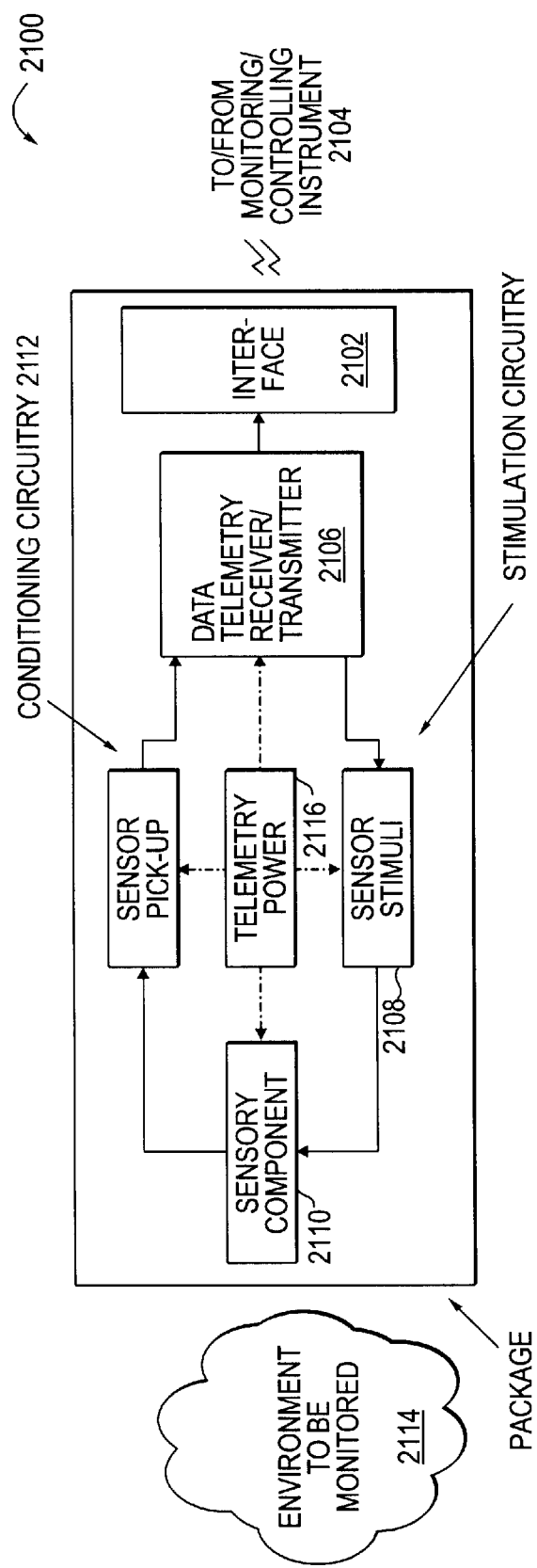
FIG. 21 is a functional block diagram of a radio frequency (RF) powered or telemetry powered hybrid sensor telemetry electrode of an embodiment.

Further alternative embodiments of the hybrid sensor telemetry electrode use radio frequency (RF) powering to remotely provide power to the hybrid sensor circuitry, thereby eliminating the battery power source. FIG. 21 is a functional block diagram of a RF powered or telemetry powered hybrid sensor telemetry electrode 2100 of an embodiment. The RF powered hybrid sensor telemetry electrode 2100 includes an interface 2102 that couples signals between circuitry of the sensor electrode and monitoring and controlling instruments 2104. The interface 2102 is coupled to the monitoring and controlling instruments 2104 using a wireless interface or network, but is not so limited. The interface 2102 is coupled to a data telemetry transmitter/ receiver (transceiver) 2106 of the sensor electrode, but is not so limited.

The transceiver 2106 is coupled to sensory circuitry including stimulation circuitry 2108, or sensor stimuli circuitry, sensory components 2110, and conditioning circuitry 2112, or sensor pick-up circuitry. The stimulation circuitry 2108 and the conditioning circuitry 2112 are coupled to a sensory component 2110 that receives signals or data from the environment 2114 that is being monitored. A telemetry power source 2116 is coupled to each of the transceiver 2106, stimulation circuitry 2108, sensory component 2110, and conditioning circuitry 2112.

Figure 22:
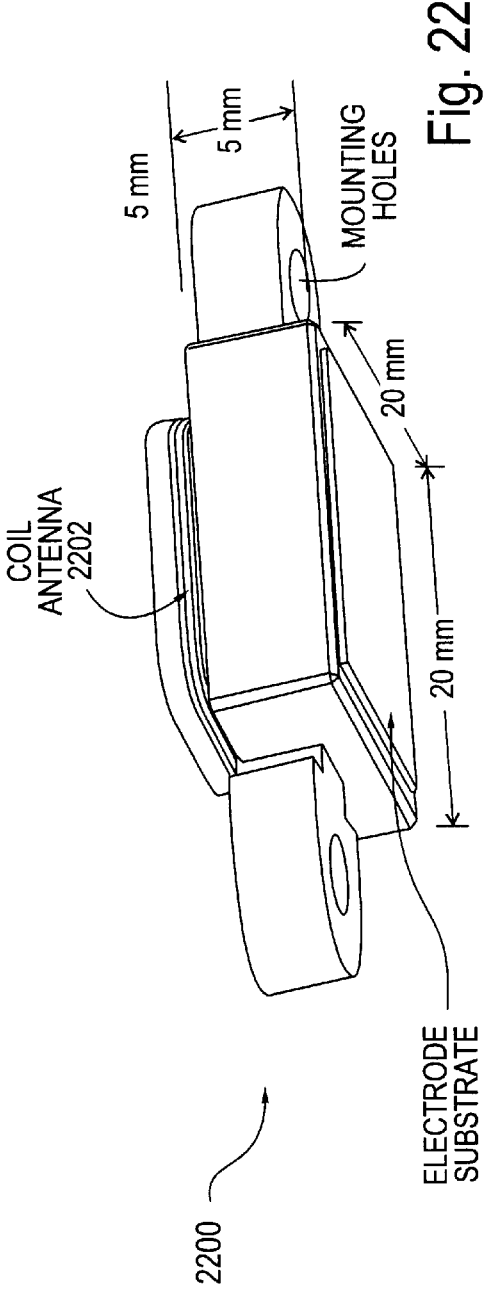
FIG. 22 is a hybrid sensor electrode of an embodiment having a telemetry system and a coil antenna.

FIG. 22 is a hybrid sensor electrode 2200 of an embodiment having a telemetry system and a coil antenna 2202. The coil antenna 2202 is used to communicate with the electrode 2200 and to provide power to the electrode 2200, thereby eliminating batteries as an electrode power source.

The transceiver section of a RF powered hybrid sensor telemetry electrode of an embodiment is coupled to an antenna that optimizes the performance of the link while providing reduced size, weight, and cost. The antenna types are configured for use with frequencies in the range of 1 kHz to 6 GHz. The antenna types used in a hybrid sensor electrode of an embodiment can be either a flat antenna, a spiral antenna, or an array antenna.

Figure 23:
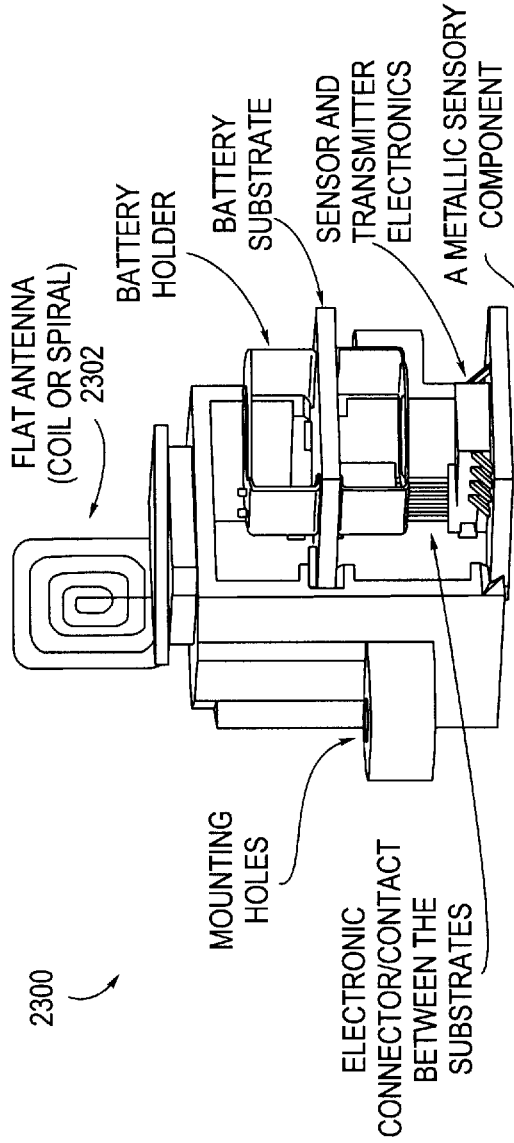
FIG. 23 is a hybrid sensor electrode of an embodiment with a flat antenna.

FIG. 23 is a hybrid sensor electrode 2300 of an embodiment with a flat antenna 2302. A flat antenna 2302 of an embodiment includes an air-core transmitter antenna used for transmitting and receiving in a 13.56 MHz system. The dimensions of the flat antenna are approximately in the range 20 mm by 20 mm by 1 mm, but are not so limited. The range of a system link using this antenna is approximately in the range 0.5 to 1.5 meters.

Alternate embodiments of the hybrid sensor electrode may use a spiral antenna or an array antenna for transmitting and receiving at higher frequencies. A spiral antenna comprises a thick film spiral inductor embedded in a printed circuit board.

A typical sensor electrode application may impose dimensional limitations on the sensor electrode package. For example, bulky transmitter sizes may not be ideal for head mounts during sleep studies due to patient discomfort. Furthermore, heavy transmitters that often find use in high resolution electrode/EKG applications where tens of electrodes are placed on the subject could lead to patient discomfort. Moreover, the size and weight of the transmitter section limits the telemetry application area. In considering these transmitter section limitations, elimination of batteries as a sensor electrode power source would result in a reduction in the size and weight of the associated sensor electrode, with an associated increase in patient comfort. This reduction in size and weight arises from the elimination of a typical battery that has parameters including: a diameter of approximately 6 to 18 mm; a thickness of approximately 6 mm; a weight of approximately less than 100 mg; and, a life approximately in the range of one day to 6 months.

The hybrid sensor electrode of an embodiment eliminates the requirement for a local battery by using remote powering, also referred to as telemetry powering, infrared (IR) powering, or RF powering. The remote powering is provided over ranges in excess of one meter. Thus, each receiver section will not only be able to communicate with eight transmitters section, but also will have the capability to remotely power the transmitters via the transmitter antenna.

Figure 24:
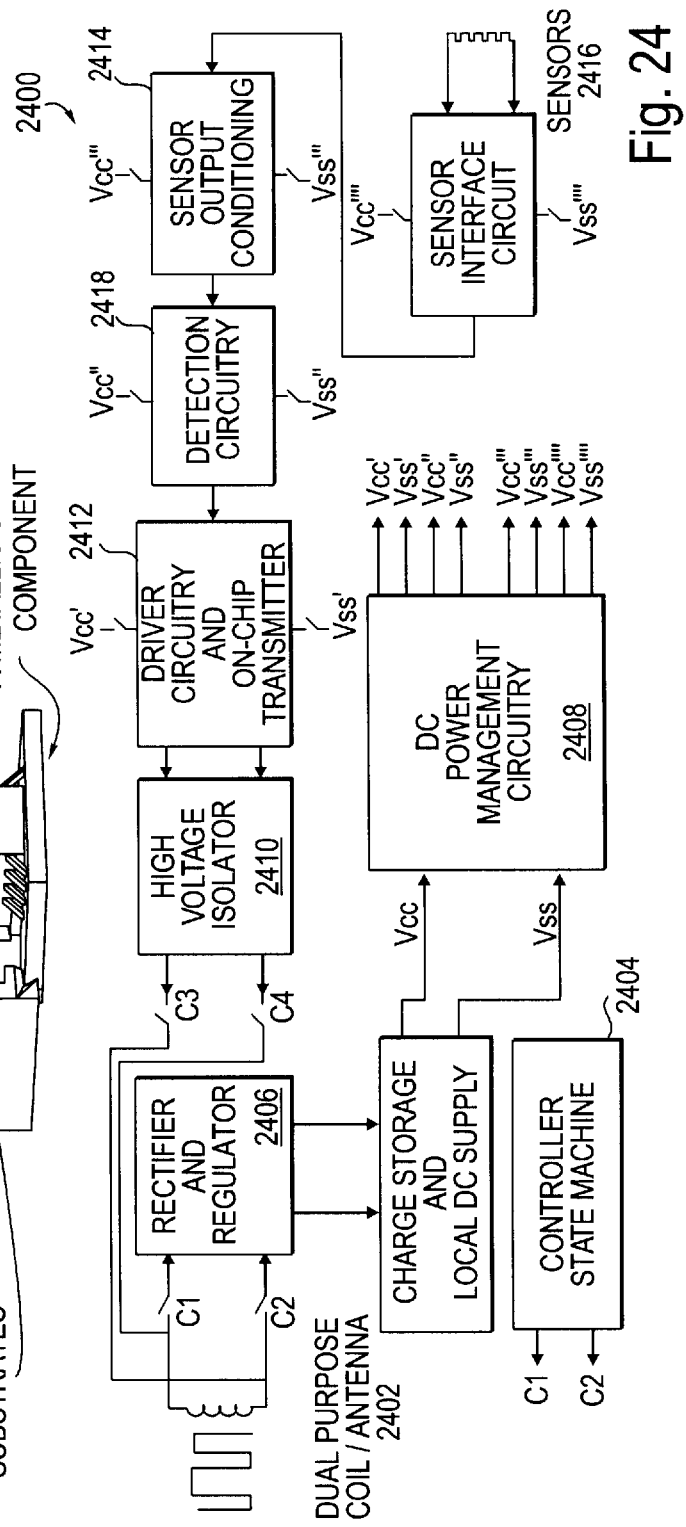
FIG. 24 is a block diagram of integrated circuitry (IC) of a hybrid sensor electrode transmitter section of an embodiment using telemetry powering.
Figure 25:
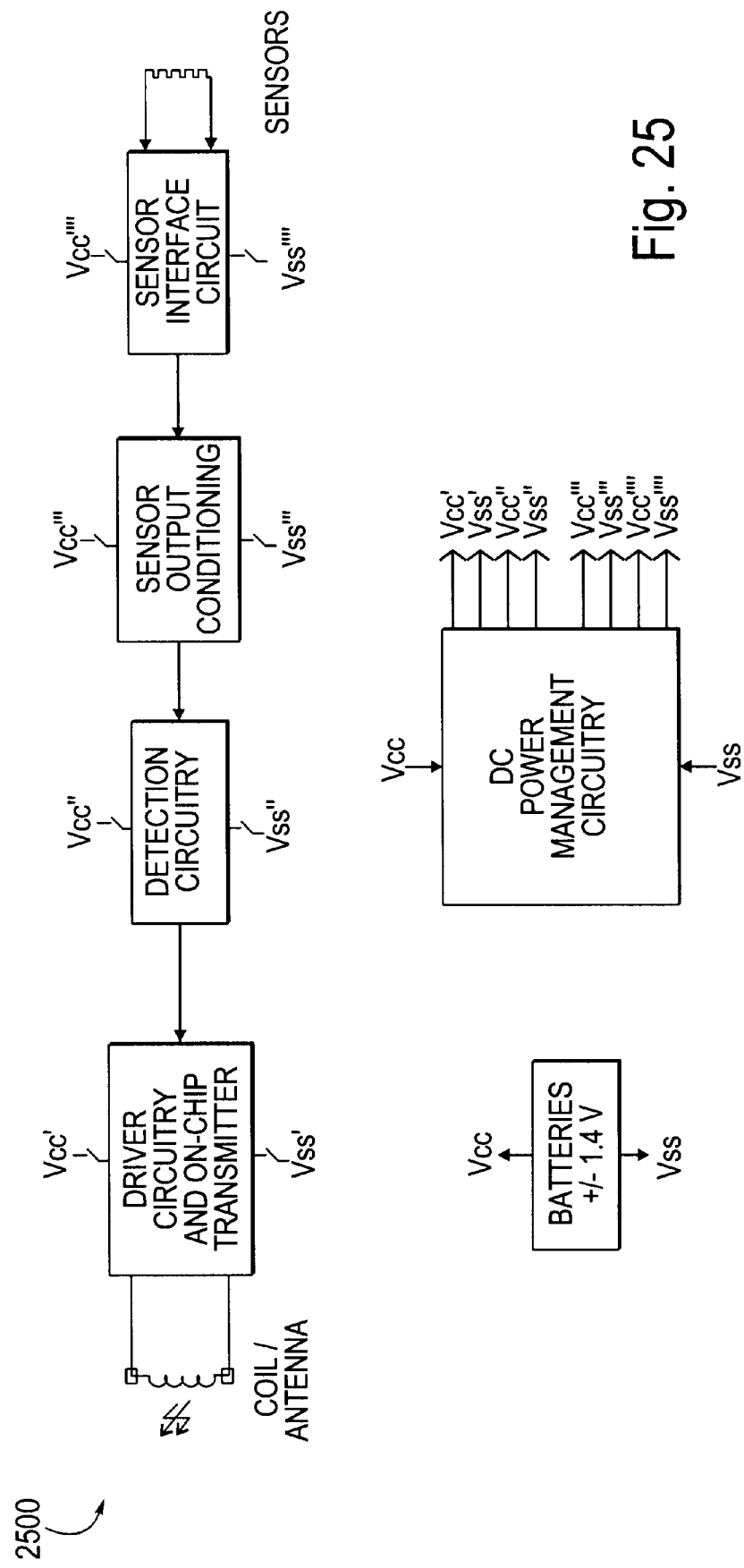
FIG. 25 is a block diagram of integrated circuitry (IC) of a hybrid sensor electrode transmitter section of an embodiment using internal battery power.

FIG. 24 is a block diagram of integrated circuitry (IC) 2400 of a hybrid sensor electrode transmitter section of an embodiment using telemetry powering. FIG. 25 is a block diagram of integrated circuitry (IC) 2500 of a hybrid sensor electrode transmitter section of an embodiment using internal battery power. These ICs 2400 and 2500 provide reduced size, weight, power, and cost with an associated benefit of higher levels of integrated functionality. Furthermore, these ICs 2400 and 2500 provide the ability to inject low current to measure skin impedance, and to allow intra-electrode communication for noise reduction and noise cancellation. The ICs of an embodiment use 0.8 micrometer complementary metal-oxide semiconductor (CMOS) technology, but are not so limited.

The ICs 2400 and 2500 are partitioned based on functionality, wherein the functional partitions include power management circuitry, power conditioning circuitry, transmitter circuitry, and sensor conditioning circuitry, but are not so limited. In an embodiment, each section of the IC can be tested separately and disabled from outside pins, allowing for full or partial utilization of the IC as needed. For example, the remote power detection circuitry is part of the power conditioning section. Provisions are made via additional bonding pads and power switching mechanisms wherein this circuitry can be disabled so that all other sections of the IC can be tested separately.

In operation, with reference to FIG. 24, a large alternating current (AC) signal is received by the dual-purpose coil/antenna 2402. The AC signal is converted into a regulated direct current (DC) voltage, which supplies power to the local components. Initially, the controller state machine 2404 momentarily closes switches C1 and C2, while switches C3 and C4 remain open. This allows the incoming AC signal to be rectified and regulated into a DC voltage. In an embodiment, the rectifier and regulator 2406 converts an AC signal to a DC signal and regulates the voltages for the entire IC. The regulated DC voltage is stored for local DC distribution to the rest of the circuit.

Prior to DC power distribution, the DC power management circuitry 2408 optimizes power consumption by prioritizing power to the components. The power manager/controller 2408 supervises the instantaneous power on the bus, and determines which section of the circuit has priority for utilizing the power. According to a round robin mechanism, the power manager/controller 2408 turns segments of the circuit on or off to optimize power consumption.

When the charge storage operation is completed, the controller state machine 2404 simultaneously opens C1 and C2, while closing C3 and C4 to allow electrode/EKG data to be transmitted. The high voltage isolator 2410 prevents large signals that may perturb the driver and transmitter circuitry 2412. The sensor output conditioning circuit 2414 generates programmable pulsed current of 1 microamp (uA) to 100 uA in amplitude and delivers it to the sensor 2416. The sensor output conditioning circuitry 2414 amplifies, filters and biases the electrode/EKG signal to be sent to the transmitter. The detection-controller circuitry 2418 determines whether the signal level is that of an electrode or EKG, and conditions the signal to prevent saturation of the transmitter circuitry. Upon completion of data transmission, the process of remote powering and data transmission is repeated.

As a result of advances made in the areas of micromachining, integrated circuit technology, and printed wiring board capabilities, the cost difference between active electrodes of an embodiment and wet surface electrodes is negligible. Furthermore, the superior performance of the active electrodes of an embodiment allow for their use in new application areas that demand higher performance and a higher number of electrodes than their wet counterparts. For example, long term (over 24 hours) recording and embedded telemetry are provided, and applications such as biofeedback (use of sensors and computers to improve or control deficiencies), sleep monitoring (analyzing sleep patterns and disorders), alertness monitoring (monitoring the mental awareness of a person), biocontrol games (input and output form the biology to computer and video games), and biocontrol of computers are enabled.

Figure 26:
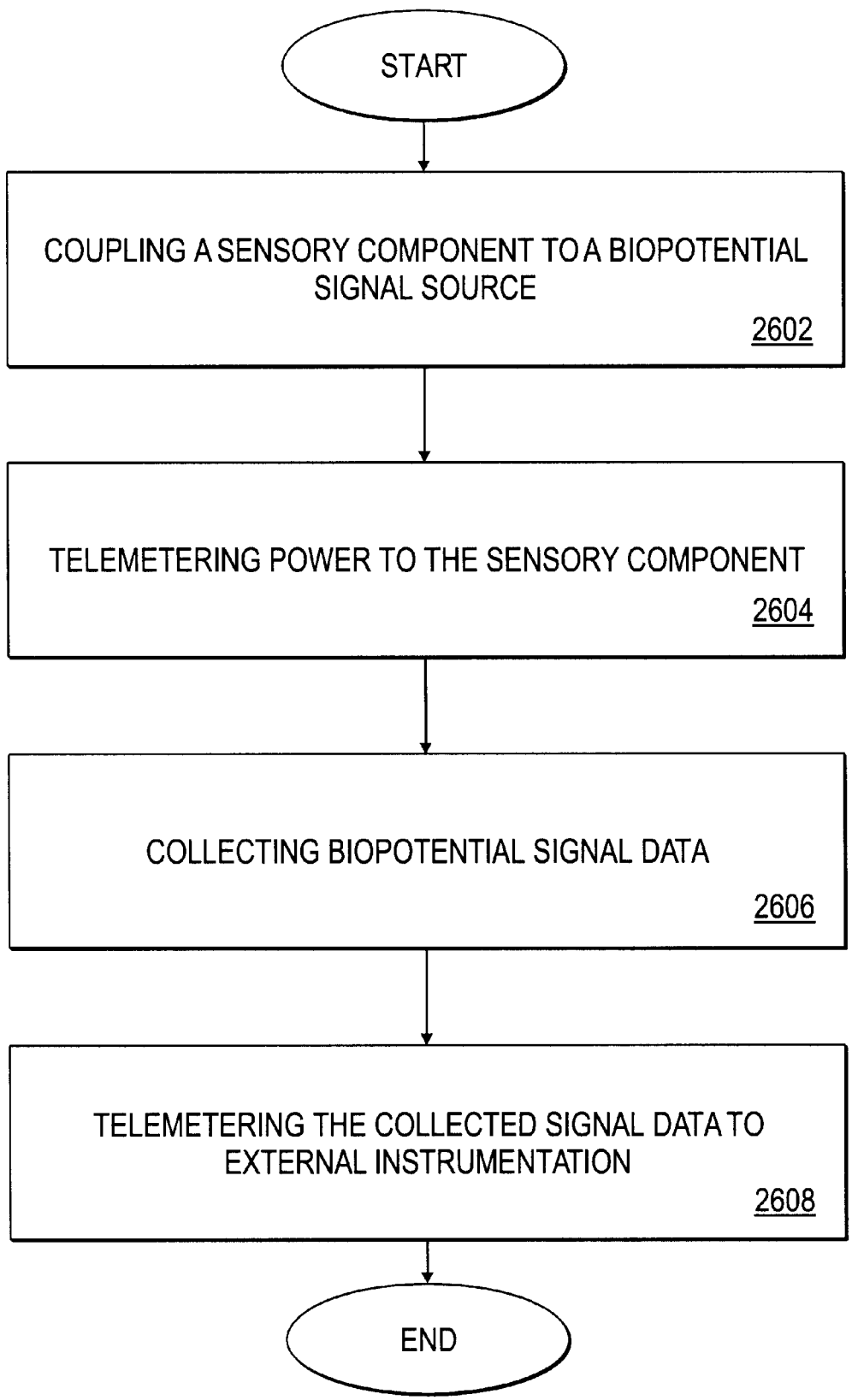
FIG. 26 is a flowchart of a method for collecting biopotential signals of an embodiment.

FIG. 26 is a flowchart of a method for collecting biopotential signals of an embodiment. Operation begins at step 2602, where at least one sensory component or element is capacitively coupled to a biopotential signal source. Power is telemetered to and received by the sensory component, at step 2604. Biopotential signals and data are collected, at step 2606, and the collected signals and data are telemetered to external instrumentation, at step 2608.

The foregoing description of various embodiments of the claimed invention is presented for purposes of illustration and description. It is not intended to limit the claimed invention to the precise forms disclosed. Many modifications and equivalent arrangements may be apparent.

What is claimed is:

1. A biopotential sensor electrode system for use with external instrumentation to measure a biopotential of a patient, comprising:

at least one biopotential sensor electrode coupled to at least one telemetry component, the at least one biopotential sensor electrode including at least one sensory component adapted to engage the skin of the patient and sense biopotential signals, the at least one sensory component having first and second layers of electrically conductive material and a dielectric layer disposed between the first and second layers of electrically conductive material; and at least one receiver section comprising at least one receiver, the at least one receiver section receiving biopotential signals from the at least one telemetry component for transfer to the external instrumentation.

2. The biopotential sensor electrode system of claim 1, wherein the at least one biopotential sensor electrode further comprises:

at least one conditioning component coupled to the at least one sensory component;

at least one interface coupled to the at least one conditioning component; and at least one power source coupled among the at least one sensory component, the at least one conditioning component, and the at least one interface.

3. The biopotential sensor electrode system of claim 1, wherein the second layer of electrically conductive material is coupled, to the at least one conditioning component using at least one component selected from a group consisting of high voltage protection circuitry, at least one bond, at least one metal layer, at least one resistive element, charge balancing circuitry, and a feedback amplifier.

4. The biopotential sensor electrode system of claim 3, wherein the at least one bond is selected from a group consisting of a permanent metallic bond and a snap connector.

5. The biopotential sensor electrode system of claim 1, wherein the first layer of electrically conductive material is coupled to the dielectric layer through a third layer of electrically conductive material and a first bond, wherein the second layer of electrically conductive material is coupled to the dielectric layer through a fourth layer of electrically conductive material and a second bond.

6. The biopotential sensor electrode system of claim 5, wherein the first bond and the second bond are selected from a group consisting of a permanent metallic bond and a snap connector.

7. The biopotential sensor electrode system of claim 6, wherein the second layer of electrically conductive material is coupled to the at least one conditioning component using at least one component selected from a group consisting of charge balancing circuitry and at least one bond.

8. The biopotential sensor electrode system of claim 7, wherein the at least one bond is selected from a group consisting of a permanent metallic bond and a snap connector.

9. The biopotential sensor electrode system of claim 2, further comprising at least one stimulation component coupled among the at least one interface and the at least one sensory component, wherein the at least one stimulation component provides stimulation signals to the skin of the patient and includes at least one component selected from a group consisting of at least one programmable current source, at least one programmable voltage source, at least one programmable generator, at least one current-to-voltage converter, and at least one transresistance amplifier.

10. The biopotential sensor electrode system of claim 2, wherein the at least one power source comprises at least one power source selected from a group consisting of at least one battery, at least one solar cell, and a telemetry power component, wherein the telemetry power component generates power in response to telemetry signals received from the external instrumentation.

11. The biopotential sensor electrode system of claim 2, further comprising at least one bidirectional multiplexer coupled to the at least one interface to transfer signals to the external instrumentation.

12. The biopotential sensor electrode system of claim 2, wherein the at least one interface is selected from a group consisting of an analog interface and a digital interface.

13. The biopotential sensor electrode system of claim 1, wherein the at least one biopotential sensor electrode includes a plurality of biopotential sensor electrodes arranged in at least one electrode array.

14. The biopotential sensor electrode system of claim 13, further comprising at least one power source coupled among the at least one biopotential sensor electrodes of the at least one electrode array.

15. The biopotential sensor electrode system of claim 13, further comprising at least one power source for each biopotential sensor electrode of the at least one electrode array.

16. The biopotential sensor electrode system of claim 3, wherein the plurality of biopotential sensor electrodes are on a single substrate.

17. The biopotential sensor electrode system of claim 3, further comprising a network coupled to the at least one electrode array and the external instrumentation, wherein the network comprises at least one network coupling selected from a group consisting of wired, wireless, and a combination of wired and wireless.

18. The biopotential sensor electrode system of claim 1, wherein the at least one telemetry component includes a telemetry receiver for receiving power from the external instrumentation.

19. The biopotential sensor electrode system of claim 1, further comprising at least one reference link coupled to the at least one biopotential sensor electrode that allows the at least one biopotential sensor electrode to be synchronized and referenced to a single potential, wherein the at least one reference link is provided by at least one coupling selected from a group consisting of a wired link, a telemetry link, and current injection to a skin surface.

20. A biopotential sensor electrode system for use with external instrumentation to measure a biopotential of a patient, comprising:
 at least one biopotential sensor electrode having at least one signal transfer component and at least one sensory component coupled to the at least one signal transfer component and adapted to engage the skin of the patient and sense biopotential signals, wherein the at least one sensory component comprises,
  a first layer of electrically conductive material coupled to a dielectric layer;
  a second layer of electrically conductive material coupled among the dielectric layer, at least one resistive element, at least one charge balancing current source and sink, and at least one biopotential electrode circuit; and
 at least one receiver section comprising at least one receiver, the at least one receiver section receiving biopotential signals from the signal;transfer component for transfer to external instrumentation.

21. The biopotential sensor electrode system of claim 20, further comprising at least one reference link coupled to the at least one biopotential sensor electrode that allows the at least one biopotential sensor electrode to be synchronized and referenced to a single potential, wherein the at least one reference link is provided by at least one coupling selected from a group consisting of a wired link, a telemetry link, and current injection to a skin surface.

22. The biopotential sensor electrode system of claim 20, wherein the at least one biopotential sensor electrode includes a plurality of biopotential sensor electrodes arranged in at least one electrode array.

23. The biopotential sensor electrode system of claim 30, further comprising a network coupled to the at least one electrode array and the external instrumentation, wherein the network comprises at least one network coupling selected from a group consisting of wired, wireless, and a combination of wired and wireless.

24. A biopotential sensor electrode system for use with external instrumentation to measure a biopotential of a patient, comprising:
 at least one biopotential sensor electrode having at least one signal transfer component and at least one sensory component coupled to the at least one signal transfer component and adapted to engage the skin of the patient and sense biopotential signals, wherein the at least one sensory component comprises,
  a first layer of electrically conductive material coupled to a dielectric layer and voltage protection circuitry;
  a second layer of electrically conductive material coupled among the dielectric layer, at least one biopotential electrode circuit, and at least one charge balancing circuit; and
 at least one receiver section comprising at least one receiver, the at least one receiver section receiving biopotential signals from the signal transfer component for transfer to the external instrumentation.

25. The biopotential sensor electrode system of claim 24, further comprising at least one reference link coupled to the at least one biopotential sensor electrode that allows the at least one biopotential sensor electrode to be synchronized and referenced to a single potential, wherein the at least one reference link is provided by at least one coupling selected from a group consisting of a wired link, a telemetry link, and current injection to a skin surface.

26. The biopotential sensor electrode system of claim 24, wherein the at least one biopotential sensor electrode includes a plurality of biopotential sensor electrodes arranged in at least one electrode array.

27. The biopotential sensor electrode system of claim 26, further comprising a network coupled to the at least one electrode array and the external instrumentation, wherein the network comprises at least one network coupling selected from a group consisting of wired, wireless, and a combination of wired and wireless.

28. A method for collecting biopotential signals from a patient, comprising:
 transferring telemetry signals containing power signals from external instrumentation to at least one sensor electrode engaged with the skin of the patient;

generating power for the sensor electrode in response to the power signals;

receiving and conditioning biopotential signals from the skin with the sensor electrode to produce conditioned biopotential signals;

providing stimulation signals to the skin to measure the impedance of the skin; and receiving telemetered conditioned biopotential signals at the external instrumentation.

29. The method of claim 28, where in the receiving and conditioning step includes the step of capacitively coupling the sensor electrode to the skin of the patient.

30. A computer readable medium containing executable instructions which, when executed in a processing system, causes the system to collect biopotential signals from a patient, the collection comprising:

transferring telemetry signals containing power signals from external instrumentation to at least one sensor electrode engaged with the skin of the patient;

generating power for the sensor electrode in response to the power signals;

receiving and conditioning biopotential signals from the skin with the sensor electrode to produce conditioned biopotential signals;

providing stimulation signals to the skin;

measuring the impedance of the skin; and receiving telemetered conditioned biopotential signals at the external instrumentation.

31. The computer readable medium of claim 30, wherein the collection comprises dynamically measuring the impedance of the skin.

32. An electromagnetic medium containing executable instructions which, when executed in a processing system, causes the system to collect biopotential signals from a patient, the collection comprising:

transferring telemetry signals containing power signals from external instrumentation to at least one sensor electrode engaged with the skin of the patient;

generating power for the sensor electrode in response to the power signals;

receiving and conditioning biopotential signals from the skin with the sensor electrode to produce conditioned biopotential signals;

providing stimulation signals to the skin surface to measure the impedance of the skin; and receiving telemetered conditioned biopotential signals at the external instrumentation.

33. The electronic medium of claim 32, wherein the collection comprises providing stimulation signals to the skin surface to dynamically measure the impedance of the skin.

34. A biopotential sensor electrode system from a patient, comprising:

means for transferring telemetry signals containing power signals from external instrumentation to at least one sensor electrode engaged with the skin of the patient;

means for generating power for the sensor electrode in response to the power signals;

means for receiving and conditioning biopotential signals from the skin with the sensor electrode to produce conditioned biopotential signals;

means for providing stimulation signals to the skin surface to measure the impedance of the skin; and means for receiving telemetered conditioned biopotential signals at the external instrumentation.

35. The biopotential electrode system of claim 34, wherein the means for providing stimulation to the skin includes means for providing stimulation signals to the skin surface to dynamically measure the impedance of the skin.

* * * * *